United States Patent
Morrisey et al.

(10) Patent No.: US 12,128,136 B2
(45) Date of Patent: Oct. 29, 2024

(54) COMPOSITIONS AND METHODS FOR CARDIAC REGENERATION

(71) Applicant: THE TRUSTEES OF THE UNIVERSITY OF PENNSYLVANIA, Philadelphia, PA (US)

(72) Inventors: Edward E. Morrisey, Newtown Square, PA (US); Jason A. Burdick, Philadelphia, PA (US); Leo Wang, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 16/499,618

(22) PCT Filed: Apr. 2, 2018

(86) PCT No.: PCT/US2018/025652
§ 371 (c)(1),
(2) Date: Sep. 30, 2019

(87) PCT Pub. No.: WO2018/183997
PCT Pub. Date: Oct. 4, 2018

(65) Prior Publication Data
US 2020/0108013 A1    Apr. 9, 2020

Related U.S. Application Data

(60) Provisional application No. 62/479,908, filed on Mar. 31, 2017.

(51) Int. Cl.
*A61K 9/06* (2006.01)
*A61K 31/7105* (2006.01)
*A61K 47/36* (2006.01)
*A61P 9/04* (2006.01)

(52) U.S. Cl.
CPC ............ *A61K 9/06* (2013.01); *A61K 31/7105* (2013.01); *A61K 47/36* (2013.01); *A61P 9/04* (2018.01)

(58) Field of Classification Search
CPC ...... A61K 9/06; A61K 31/7105; A61K 47/36; A61P 9/04
See application file for complete search history.

(56) References Cited

U.S. PATENT DOCUMENTS

| | | |
|---|---|---|
| 2009/0246875 A1 | 10/2009 | Yamanaka et al. |
| 2013/0035374 A1 | 2/2013 | Morrisey |
| 2015/0202299 A1* | 7/2015 | Burdick ................ A61L 31/145 424/85.2 |

FOREIGN PATENT DOCUMENTS

| | | | |
|---|---|---|---|
| WO | WO/2009/091659 | | 7/2009 |
| WO | WO 2014/028209 A1 | | 2/2014 |
| WO | WO 2015/175889 | * | 11/2015 |
| WO | WO 2015/175889 A1 | | 11/2015 |

OTHER PUBLICATIONS

Rodell et al. Biomacromolecules. 2013; 14(11): 20 pages. (Year: 2013).*
Baumann et al., "miRNA-based therapies: strategies and delivery platforms for oligonucleotide and non-oligonucleotide agents." Future medicinal chemistry 6.17 (2014): 1967-1984.
Eulalio et al. "Functional screening identifies miRNAs inducing cardiac regeneration." Nature 492.7429 (2012): 376-381.
European Search Report from European Application No. 18777670.3 dated Nov. 5, 2020.
Gaffey et al., "Injectable shear-thinning hydrogels used to deliver endothelial progenitor cells, enhance cell engraftment, and improve ischemic myocardium." The Journal of thoracic and cardiovascular surgery 150.5 (2015): 1268-1277.
Mealy et al., "Sustained small molecule delivery from injectable hyaluronic acid hydrogels through host-guest mediated retention." Journal of Materials Chemistry B 3.40 (2015): 8010-8019.
Ouyang et al. "3D printing of shear-thinning hyaluronic acid hydrogels with secondary cross-linking." ACS Biomaterials Science & Engineering 2.10 (2016): 1743-1751.
Rodell et al. "Injectable shear-thinning hydrogels for minimally invasive delivery to infarcted myocardium to limit left ventricular remodeling." *Circulation: Cardiovascular Interventions* 9.10 (2016): e004058, pp. 1-19.
Rodell et al. "Shear-thinning supramolecular hydrogels with secondary autonomous covalent crosslinking to modulate viscoelastic properties in vivo." Advanced functional materials 25.4 (2015): 636-644.
Rodell et al., "Selective Proteolytic Degradation of Guest-Host Assembled, Injectable Hyaluronic Acid Hydrogels." ACS Biomaterials Science and Engineering, vol. 1, No. 4, Mar. 9, 2015, pp. 227-286.
Seif-Naraghi et al. "Safety and efficacy of an injectable extracellular matrix hydrogel for treating myocardial infarction." Science translational medicine 5.173 (2013): 173ra25, pp. 1-13.
Tian et al. "A microRNA-Hippo pathway that promotes cardiomyocyte proliferation and cardiac regeneration in mice." Science translational medicine 7.279 (2015): 279ra38-279ra38.

(Continued)

*Primary Examiner* — David Browe
(74) *Attorney, Agent, or Firm* — Mark S. Cohen; PEARL COHEN ZEDEK LATZER BARATZ LLP

(57) ABSTRACT

The present disclosure provides microRNA-based therapies using a hydrogel delivery system that provides regenerative approach to myocardial infarction by targeting cardiomyocytes. The hydrogel provides for local and sustained cardiac delivery of microRNAs, such miR-302 mimics that can be used to promote cardiomyocyte proliferation. Also provided are compositions suitable for local and sustained release and methods for intramyocardial gel delivery of a miRNA oligonucleotide.

18 Claims, 44 Drawing Sheets
Specification includes a Sequence Listing.

(56) References Cited

OTHER PUBLICATIONS

Rodell et al., Rational Design of Network Properties in Guest-Host Assembled and Shear-Thinning Hyaluronic Acid Hydrogels., J Mater Chem B Mater Biol Med., Nov. 11, 2013, vol. 14, No. 11, pp. 125-134.
International Search Report for PCT/US18/25652 dated Jun. 18, 2018.

* cited by examiner

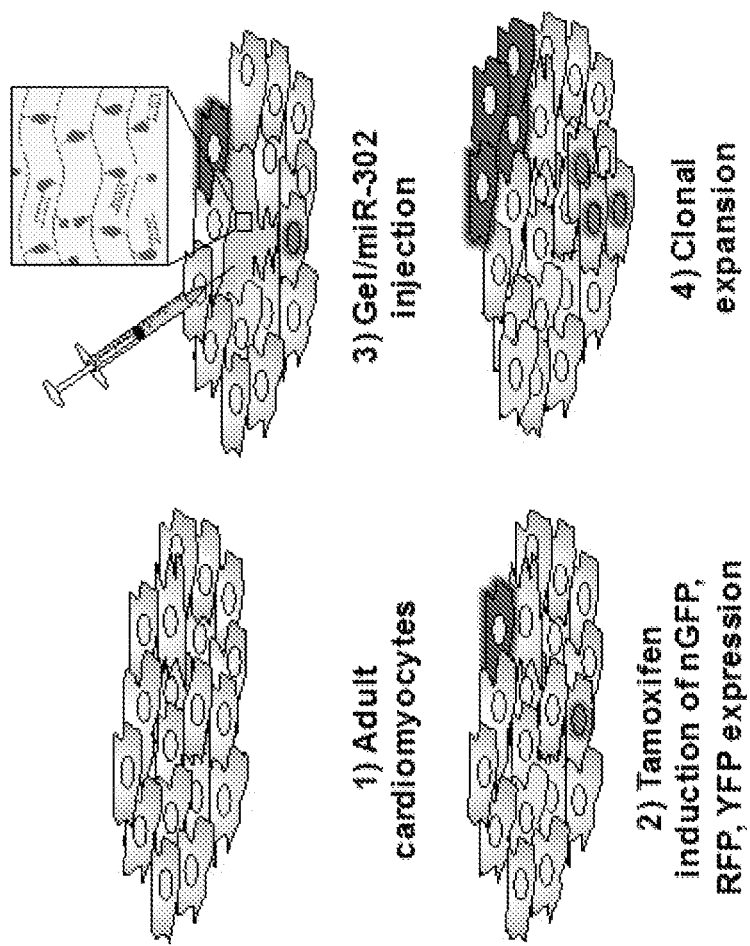

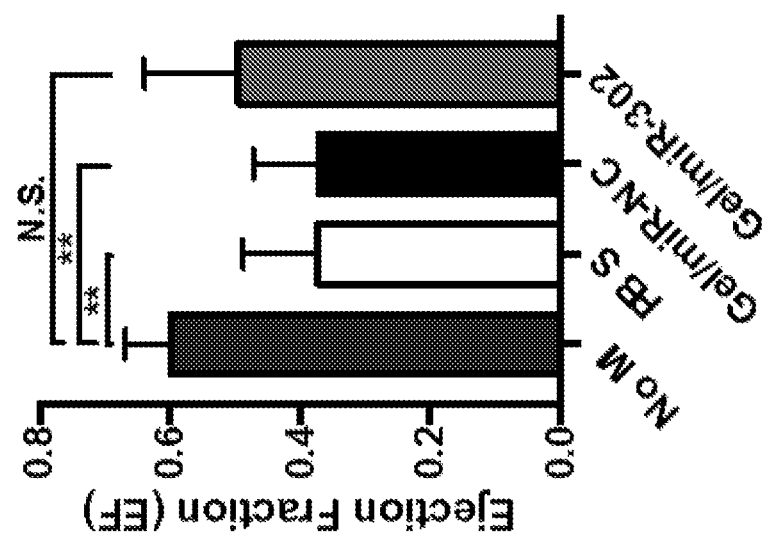

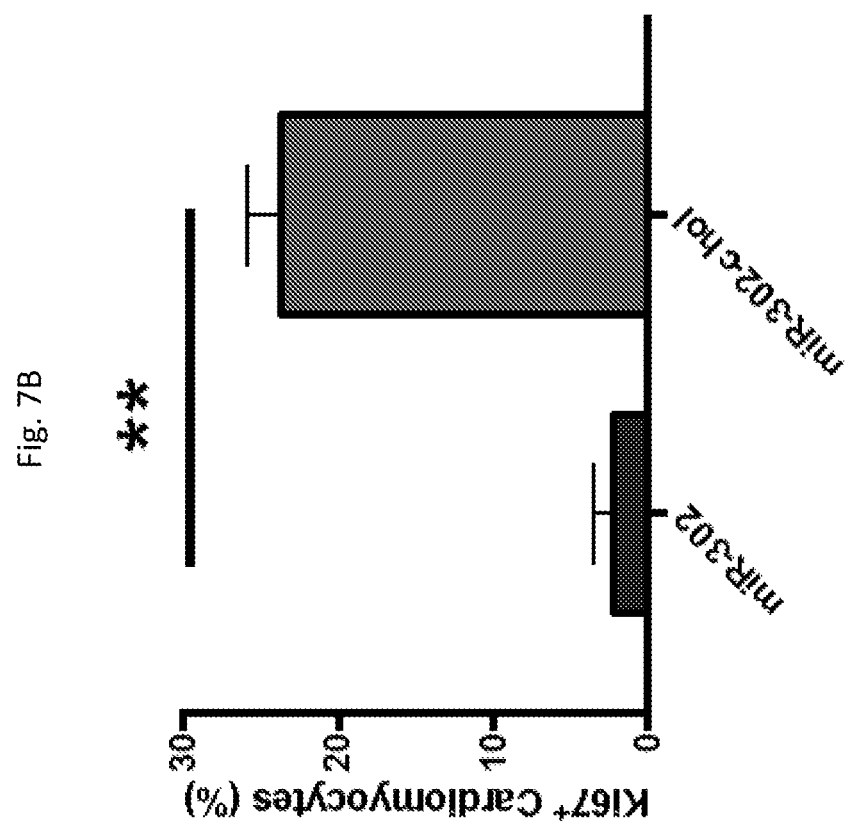

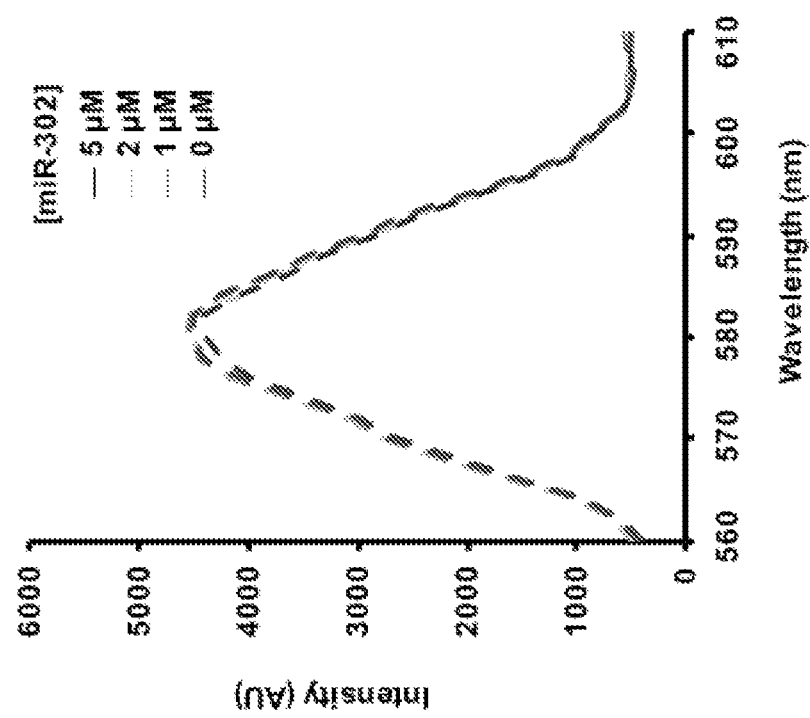

Fig. 8D

Benesi-Hildebrand Equation:

$$\frac{1}{\triangle Em_{550}} = \frac{1}{K_a \triangle Em_{580max}} * \frac{1}{[miR\text{-}302\text{-}chol]} + \frac{1}{\triangle Em_{580max}}$$

$$\frac{1}{\triangle Em_{580max}} = 0.0008681 \text{ nm}^{-1} \qquad \frac{1}{K_a \triangle Em_{580max}} = 0.0004342 \text{ }\mu M/nm$$

$$K_a = 2 \times 10^3 \text{ M}^{-1}$$

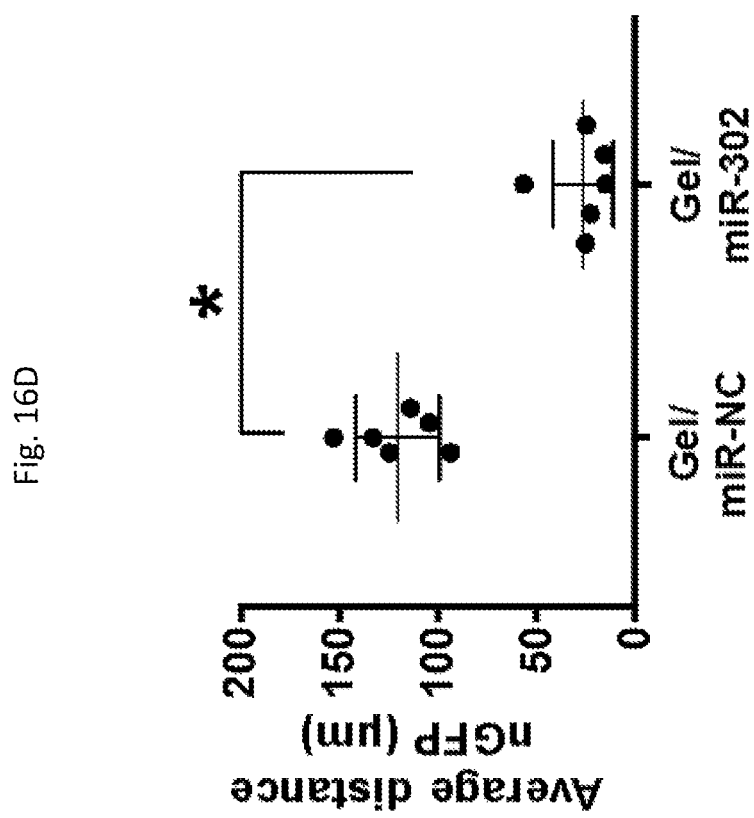

SEQUENCE LISTING

```
<160> NUMBER OF SEQ ID NOS: 23

<210> SEQ ID NO 1
<211> LENGTH: 23
<212> TYPE: RNA
<213> ORGANISM: Homo sapiens

<400> SEQUENCE: 1
uaagugcuuc cauguuuuag uag                                             23

<210> SEQ ID NO 2
<211> LENGTH: 23
<212> TYPE: RNA
<213> ORGANISM: Homo sapiens

<400> SEQUENCE: 2
acuuuaacau ggaagugcuu ucu                                             23

<210> SEQ ID NO 3
<211> LENGTH: 23
<212> TYPE: RNA
<213> ORGANISM: Homo sapiens

<400> SEQUENCE: 3
uaagugcuuc cauguuucag ugg                                             23

<210> SEQ ID NO 4
<211> LENGTH: 22
<212> TYPE: RNA
<213> ORGANISM: Homo sapiens

<400> SEQUENCE: 4
uuuaacaugg ggguaccugc ug                                              22

<210> SEQ ID NO 5
<211> LENGTH: 23
<212> TYPE: RNA
<213> ORGANISM: Homo sapiens

<400> SEQUENCE: 5
uaagugguuc cauguuuugg uga                                             23

<210> SEQ ID NO 6
<211> LENGTH: 22
<212> TYPE: RNA
<213> ORGANISM: Homo sapiens

<400> SEQUENCE: 6
uaaacgugga uguacuugcu uu                                              22
```

```
<210> SEQ ID NO 7
<211> LENGTH: 23
<212> TYPE: RNA
<213> ORGANISM: Homo sapiens

<400> SEQUENCE: 7
uaagugcuuc cauguuugag ugu                                              23

<210> SEQ ID NO 8
<211> LENGTH: 22
<212> TYPE: RNA
<213> ORGANISM: Homo sapiens

<400> SEQUENCE: 8
aauugcacuu uagcaauggu ga                                               22

<210> SEQ ID NO 9
<211> LENGTH: 22
<212> TYPE: RNA
<213> ORGANISM: Homo sapiens

<400> SEQUENCE: 9
acuguugcua auaugcaacu cu                                               22

<210> SEQ ID NO 10
<211> LENGTH: 69
<212> TYPE: RNA
<213> ORGANISM: Homo sapiens

<400> SEQUENCE: 10
ccaccacuua aacguggaug uacuugcuuu gaaacuaaag aaguaagugc uuccauguuu      60
uggugaugg                                                              69

<210> SEQ ID NO 11
<211> LENGTH: 73
<212> TYPE: RNA
<213> ORGANISM: Homo sapiens

<400> SEQUENCE: 11
gcucccuuca acuuuaacau ggaagugcuu ucgugacuu uaaaaguaag ugcuuccaug       60
uuuuaguagg agu                                                         73

<210> SEQ ID NO 12
<211> LENGTH: 68
<212> TYPE: RNA
<213> ORGANISM: Homo sapiens

<400> SEQUENCE: 12
ccuuugcuuu aacauggggg uaccugcugu gugaaacaaa aguaagugcu uccauguuuc      60
aguggagg                                                               68

<210> SEQ ID NO 13
<211> LENGTH: 68
<212> TYPE: RNA
<213> ORGANISM: Homo sapiens

<400> SEQUENCE: 13
ccucuacuuu aacauggagg cacuugcugu gacaugacaa aaauaagugc uuccauguuu      60
gagugugg                                                               68

<210> SEQ ID NO 14
```

```
<211> LENGTH: 23
<212> TYPE: RNA
<213> ORGANISM: Caenorhabditis elegans

<400> SEQUENCE: 14
cgcucauucu gccgguuguu aug                                              23

<210> SEQ ID NO 15
<211> LENGTH: 24
<212> TYPE: RNA
<213> ORGANISM: Caenorhabditis elegans
<220> FEATURE:
<221> NAME/KEY: misc_feature
<222> LOCATION: (24)..(24)
<223> OTHER INFORMATION: Cholesterol moiety attached

<400> SEQUENCE: 15
agaugagaaa gauccuccaa cacu                                             24

<210> SEQ ID NO 16
<211> LENGTH: 23
<212> TYPE: RNA
<213> ORGANISM: Mus musculus

<400> SEQUENCE: 16
acuuuaacau gggaaugcuu ucu                                              23

<210> SEQ ID NO 17
<211> LENGTH: 23
<212> TYPE: RNA
<213> ORGANISM: Mus musculus
<220> FEATURE:
<221> NAME/KEY: misc_feature
<222> LOCATION: (23)..(23)
<223> OTHER INFORMATION: Cholesterol moiety attached

<400> SEQUENCE: 17
gaugauuuug uaccuucgug aau                                              23

<210> SEQ ID NO 18
<211> LENGTH: 22
<212> TYPE: RNA
<213> ORGANISM: Mus musculus

<400> SEQUENCE: 18
gcuuuaacau gggguuaccu gc                                               22

<210> SEQ ID NO 19
<211> LENGTH: 22
<212> TYPE: RNA
<213> ORGANISM: Mus musculus
<220> FEATURE:
<221> NAME/KEY: misc_feature
<222> LOCATION: (22)..(22)
<223> OTHER INFORMATION: Cholesterol moiety attached

<400> SEQUENCE: 19
ggugacuuug uaccuucgug aa                                               22

<210> SEQ ID NO 20
<211> LENGTH: 21
<212> TYPE: DNA
<213> ORGANISM: Mus musculus

<400> SEQUENCE: 20
cgtttcctga gcatacctgg a                                                21
```

```
<210> SEQ ID NO 21
<211> LENGTH: 20
<212> TYPE: DNA
<213> ORGANISM: Mus musculus

<400> SEQUENCE: 21
attctcccac cgtcagtacg                                               20

<210> SEQ ID NO 22
<211> LENGTH: 21
<212> TYPE: DNA
<213> ORGANISM: Mus musculus

<400> SEQUENCE: 22
aaagtcgctc tgagttgtta t                                             21

<210> SEQ ID NO 23
<211> LENGTH: 20
<212> TYPE: DNA
<213> ORGANISM: Mus musculus

<400> SEQUENCE: 23
ccagatgact acctatcctc                                               20
```

COMPOSITIONS AND METHODS FOR CARDIAC REGENERATION

CROSS-REFERENCE TO RELATED APPLICATIONS

The subject Application is a U.S. national stage application under 37 U.S.C. 371 of PCT international Application PCT/US2018/025652, filed 2 Apr. 2018, which claims priority to U.S. Provisional Application No. 62/479,908, filed 31 Mar. 2017, the contents of which is hereby incorporatedby reference in their entirety.

GOVERNMENT INTEREST STATEMENT

This invention was made with government support under grant numbers HL100405 and HL134255 awarded by the National Institutes of Health. The government has certain rights in the invention.

FIELD OF THE INVENTION

The disclosure is directed to methods and compositions for improving cardiac function, particularly after cardiac insult such as myocardial infarction. The compositions include guest-host hydrogels adapted to provide sustained release of microRNA for certain periods of time. The microRNAs stimulate cardiac cell proliferation and restore cardiac function.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PERA_001_01WO_SeqList_ST25.txt, date recorded: Mar. 27, 2018, file size 5 kilobytes).

BACKGROUND

In the United States, heart disease is the leading cause of mortality and accounts for over 600,000 deaths a year. Myocardial infarctions (MI), or heart attacks, are individually linked to 370,000 deaths annually in the United States. Improved management of acute MI through medical and surgical innovation has allowed up to 95% of patients to survive initial hospitalization. However, many of these patients will develop chronic heart failure, resulting in a 50% mortality at five years post-MI.

While a variety of therapeutic approaches have been used to prevent heart attacks, they remain a public health issue. Preventative measures reduce the incidence of heart attacks, but after an initial heart attack, the heart tissue is damaged and a major challenge is the limited capacity for renewal of cardiomyocytes in the adult heart. Accordingly, there remains a need in the art for therapies to treat heart attack victims and other patients with cardiac injuries such that cardiac function is restored.

MircroRNAs have acquired increasing attention with respect to therapy in recent years. MicroRNAs (miRNAs) are small endogenous RNA molecules (about 21-25 nt) that regulate gene expression by targeting one or more mRNAs for translational repression or cleavage. They are small inhibitory RNAs capable of suppressing the translation of target genes with high complementarity. Several thousand miRNAs have been identified in organisms as diverse as viruses, worms, and primates through cloning or computational prediction.

One group or miRNAs, the miR-302-367 cluster, has high intracellular abundance and is cell type specific to embryonic stem cells. This miRNA-302-367 cluster was initially identified from cDNA libraries generated by directional cloning using size-fractionated RNA (17-26 nt) from undifferentiated hESCs (human embryonic stem cells). This cluster is codified in the human chromosome 4 and comprises nine different miRNAs co-transcribed in a polycistronic manner: miR-302a, miR-302a*, miR-302b, miR-302b*, miR-302c, miR-302c*, miR-302d, miR-367 and miR-367*. The miR-302 family contains seven miRNAs with a highly conserved 5' region. The miR-302-367 cluster was first identified to be expressed in mESC (murine ESC), hESC and in their malignant counterparts hECCs.

SUMMARY OF THE INVENTION

The application discloses guest-host hydrogel formulations for controlled release of miR-30 mimics. The hydrogels contain cyclodextrin-modified hyaluronic acid (HA) (CD-HA) and an adamantane-modified HA (AD-HA) along with a cholesterol-modified miR-302 mimic. The hydrogels are suitable for use in contractile tissue where the release profile of the miR-302 is effective to stimulate cardiomyocytes proliferating for about 7 days. Surprisingly, while the interaction between cholesterol and cyclodextrin modifies the release profile of the miR-302 mimic, including the cholesterol-modified miR-302 mimic does not disrupt the guest-host hydrogels significantly.

BRIEF DESCRIPTION OF THE FIGURES

FIG. 1. Gel assembly and miR-302 interactions.

FIG. 2. In vitro cardiomyocyte proliferation.

FIG. 4. Gel/miR-302 induced clonal expansion in vivo. FIG. 4B. Mechanism for gel/miR-302 induced clonal expansion: 1) adult cardiomyocytes are non-proliferative and incapable of dividing after ischemic injury; 2) tamoxifen is used to randomly label a small population of cardiomyocytes with one of four fluorescent reporter proteins; 3) hearts are infarcted and gel/miR-302 is injected into cardiomyocytes in the border zone; and 4) miR-302 stimulates differentiation, proliferation, and expansion of fluorescently-labeled cardiomyocytes, which pass the fluorescent protein gene onto daughter cells.

FIG. 5. Clonal expansion of Confetti-labeled cardiomyocytes.

FIG. 8. miR-302-chol interaction with CD-HA. FIG. 8C. Unmodified miR-302 does not lead to fluorescent recovery of CD-HA/Rho B complexes. FIG. 8D. The Benesi-Hildebrand equation can be used to determine the binding constant between the cholesterol-modified mimic and CD-HA, which approximates the guest-host binding affinity. At each dose of miR-302-chol, the change in fluorescence ($\Delta Em_{580}$) is calculated and plotted as $1/(\Delta Em_{580})$ on the Y-axis and $1/[miR-302-chol]$ on the X-axis.

FIG. 9. Synthesis and $^1H$ NMR Spectra of AD-HA and CD-HA.

FIG. 11. Rheology of hydrogels with miR-302-chol.

FIG. 12. Hydrogel erosion. Gels (100 μL) were formed with or without miR-302 (210 μM of miR-302b and 210 μM of miR-302c) at 5 wt % in microcentrifuge tubes. PBS was added to gels, collected over three weeks, and quantified for hyaluronic acid content via a uronic acid colorimetric assay, indicating minimal differences in erosion when the miR-302 was included (mean±SD, n=3).

FIG. 14. Yap expression. Two injections were made inferolateral to the proximal LAD without ligation of the LAD.

FIG. 16. Clonal proximity in hearts injected with gel/miR-NC compared to gel/miR-302. FIG. 16D Quantification of distance between nGFP cells from IMARIS measurements (mean±SD, n=3 animals per group, *p<0.05).

DETAILED DESCRIPTION

Figure 1A:
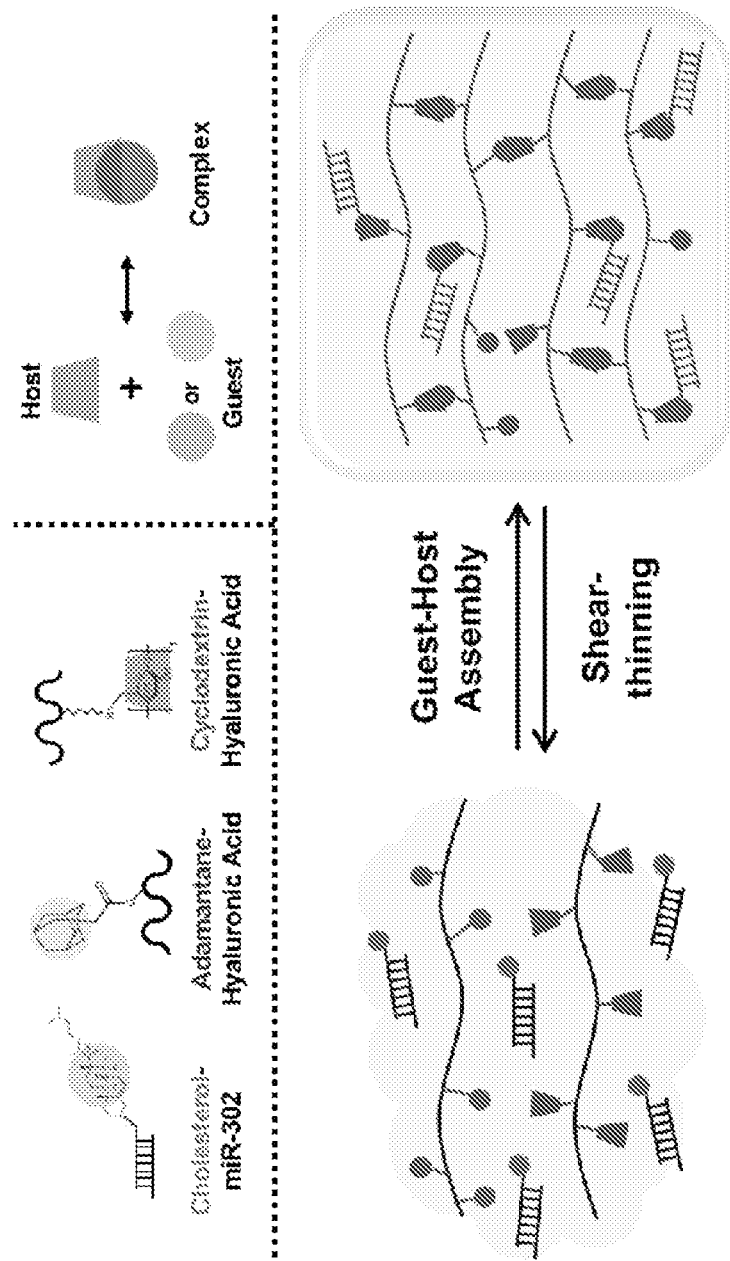
FIG. 1A HA was modified with AD or CD, which self-assemble into shear-thinning and self-healing gels. Cholesterol on miR-302-chol interacts with CD to provide a sustained release from the gel.

We have developed guest-host (GH) hydrogels capable of withstanding the rigors of cardiac muscle contractions yet remain able to deliver effective dosing of microRNA ("miRNA") modified with cholesterol to trigger cardiomyocyte proliferation in a manner that restores cardiac function in the absence of cardiomyopathy.

We previously showed that members of the polycistronic miR-302-367 cluster are important for cardiomyocyte proliferation during embryonic development by targeting members of the Hippo signal transduction pathway including Mob1b, Lats2, and Mst1.9. The result of Hippo silencing in cardiomyocytes culminates in de-phosphorylation of Yap and nuclear localization to promote transcriptional pathways that promote a de-differentiated, embryonic-like state that is highly proliferative.

Unfortunately constitutive expression miRNAs of the miR-302-367 cluster caused cardiomyopathy after myocardial infarction likely due to overproliferation and persistent de-differentiation.

Advantageously, we have now developed an approach to use guest-host hydrogels that are tolerant of the contractile nature of cardiac tissue yet release miRNAs in a dosing regimen that is appropriate to restore cardiac function after myocardial infarction. The hydrogels and dosing regimens reduce or eliminate the cardiomyopathy previously obtained.

As used herein, "about" refers to plus or minus 10% of the indicated value.

The present disclosure provided engineered hydrogel, designed for injection and sustained delivery of miR-302 that promotes both cardiomyocyte proliferation and functional regeneration. We believe this is the first report of a hydrogel being used as a carrier for a miRNA mimic for application in the regeneration of damaged cardiac tissue. Our hydrogel system was developed to overcome limitations of systemic delivery and to replace the 7 days of serial injections through sustained release from a single gel injection into the myocardium. Guest-host assembly mechanism permitted injection and self-healing to improve retention, and the cholesterol modifications did not have the expected negative impact on structure or erosion. Further, the gel can be delivered by a minimally invasive delivery methods (e.g., catheter).

To further control release, the guest-host assembly mechanism also uses cyclodextrin that can be used to sequester cholesterol-modified miRNA in the hydrogel. Interestingly, binding of cholesterol to the cyclodextrin had minimal effects on gel erosion and mechanics while sustaining the release of the miRNA mimics over three weeks in vitro, slower than when these interactions are not included. Because mimics were released faster than the gel eroded, we believe diffusion played a major role in release, likely due to the dynamic interactions within the gel and anionic repulsion between negatively charged HA and RNA. Mimic release may also be sustained due to increase in mimic size by cholesterol modification and the ability for cholesterol to aggregate with itself due to hydrophobicity, causing entrapment within the network.

In vitro, the gel/miR-302 complex led to proliferation in neonatal mouse cardiomyocytes in releasates collected as far out as 7 days. The reduction in proliferation from releasates collected after this time (D10, D15) could be due to RNA degradation given the extended time of the experiment. Remarkably, in vivo, our gel/miR-302 complex led to robust proliferation at five days in the adult heart, a terminally differentiated organ. Expression of Aurora B kinase was particularly interesting as it suggested that cardiomyocytes were not simply entering the cell cycle but actually undergoing cytokinesis. Clonal expansion of newly generated cardiomyocytes was observed surrounding the infarct zone of the hearts treated with the gel/miR-302 complex. The use of a multi-colored lineage reporter allowed us to verify the generation of new cardiomyocytes in comparison to simply observing an increase in proliferative markers (e.g., Ki67 and pH3). Our findings concur with recent data showing that the small number of newly generated cardiomyocytes that are observed over the lifespan of mammals or after injury are due to proliferation of pre-existing cardiomyocytes rather than arising from a progenitor population.[37] While the new cells themselves may enhance contractility after MI, cardiomyocytes also play a role in limiting remodeling by signaling through paracrine factors to fibroblasts. This explains the improvements in global cardiac volumes and cardiac function observed after delivery of the gel/miR-302 complex.

The proliferative potential of the gel/miR-302 complex that leads to newly-generated cardiomyocytes can be attributed to an enhancement in the retention of miR-302 mimics upon intramyocardial injection, particularly as there was minimal proliferation when gels were not included. These results are in line with our previous data showing that systemic application of miR-302 promotes cardiomyocyte proliferation during the first week. Complexing the miRNA with the gel also likely protected the double stranded miRNA mimics from degradation by ubiquitous RNAse H mediated mechanisms, allowing for the continuous and persistent release of active mimics. This work also builds on previous reports of intramyocardial miRNA mimic injections, where miRNAs were injected naked or in a lipid complex with a transfection reagent. Since gels allow for a single application and have been well-tolerated in human trials, we believe the use of a gel/miRNA complex offers significant advantages to these other approaches.

We provide a bioengineered miRNA delivery approach to promote cardiomyocyte proliferation and cardiac regeneration after MI. We believe that this is the first report of in vivo delivery of a miRNA mimic to cardiac tissue using a gel complex. This delivery mechanism has distinct advantages over current methods including: (i) overcoming the short lifespan of injected mimics, (ii) use as a single application, (iii) optimization of release of miRNA mimics over times for promoting cardiomyocyte proliferation and cardiac regeneration, and (iv)potential for adaptation to percutaneous delivery through catheter. Currently, there are no approved treatments that regenerate myocardium; in this regard, our system may have unique advantages to other existing treatments for ischemic injury.

Guest Host Hydrogels

Disclosed herein are hydrogels that locally retain and release cholesterol-modified miR302 mimics in the heart, improving efficiency and preventing proliferative signals from perturbing cellular homeostasis in other organs. The hydrogels sustain miR302 release over one week to provide a transient delivery needed to improve function after ischemic injury yet prevent cardiomyopathy arising from excessive proliferation and dedifferentiation.

The hydrogel delivery approach combines an appropriate dosing regimen with locally restricted release of the miRNAs using the hydrogel to enhance retention of miR-302 mimics upon intramyocardial injection. Retention upon injection is a major challenge to cardiac delivery of various therapeutics, owing to its highly contractile nature. The hydrogels disclosed herein increase the bioavailability of the miR-302 mimics at the appropriate site, while providing a dose that does not induce cardiomyopathy. In addition to localizing the miR-302, the hydrogel may act to protect against degradation which in turns increases their ability to interact with cells in a continuous and persistent fashion to promote advantageous cardiomyocytes proliferation in the adult.

To prepare gels, HA is modified with β-cyclodextrin (CD, host) or adamantane (Ad, guest). CD and Ad interact through guest-host chemistry in which non-covalent, hydrophobic interactions drive the molecular complexation of the two in a defined structural arrangement with high affinity ($K_a \sim 1 \times 10^5$ M−1). In preferred aspects, CD-HA modification is about 20% and AD-HA modification are about 20%.

In particular aspects, the gels are ~5% w/w. For example, gels disclosed herein may contain 3.2 mg CD-HA and 2.1 mg AD-HA for 100 μL of gel to arrive at ~5% w/w. In other aspects, the range may be about 4% or about 6%. The ratio of CD-HA to AD-HA polymers may range from about 2:3 to about 3:2.

In some aspects, CD-HA and AD-HA polymers are sterilized under UV irradiation in our cell culture hood for 1 hour. In an exemplary approach, to make 100 μL gels, the dry polymers are each resuspended in 20 μL of miR-302b and 20 uL of miR-302c each at 525 μM (dissolved in deionised water). 10 μL of PBS are added to CD-HA and AD-HA so the final volume of CD-HA and AD-HA is 50 μL (20 uL miR-302b, 20 μL of miR-302c, 10 μL of PBS). Then, gels are mixed by injecting the two components between two insulin syringes multiple times before centrifuging at max speed to get rid of air bubbles. The volume of gel obtained may be scaled up.

Additional general information regarding the array of possible hydrogel variants can be found. See e.g., Rodell, C. B. et al. "Shear-Thinning Supramolecular Hydrogels with Secondary Autonomous Covalent Crosslinking to Modulate Viscoelastic Properties In Vivo," Adv. Funct. Mater. 25, 636-644 (2014); Rodell et al. "Rational Design of Network Properties in Guest-Host Assembled and Shear-Thinning Hyaluronic Acid Hydrogels," Biomacromolecules 14, 4125-4134 (2013): Rodell, et al. "Injectable Shear-Thinning Hydrogels for Minimally Invasive Delivery to Infarcted Myocardium to Limit Left Ventricular Remodeling," Circ. Cardiovasc. Interv. 9, (2016); Seif-Naraghi, S. B. et al. "Safety and efficacy of an injectable extracellular matrix hydrogel for treating myocardial infarction," Sci. Transl.

Med. 5, 173ra25 (2013); Ouyang et al., "3D Printing of Shear-Thinning Hyaluronic Acid Hydrogels with Secondary Cross-Linking," ACS Biomater. Sci. Eng. acsbiomaterials.6b00158 (2016). doi:10.1021/acsbiomaterials.6b00158; Mealy, et al., "Sustained small molecule delivery from injectable hyaluronic acid hydrogels through host-guest mediated retention" J. Mater. Chem. B 3, 8010-8019 (2015); Gaffey et al. Injectable shear-thinning hydrogels used to deliver endothelial progenitor cells, enhance cell engraftment, and improve ischemic myocardium," J. Thorac. Cardiovasc. Surg. 150, 1268-77 (2015).

Briefly, when CD-modified HA polymers are mixed with Ad-modified HA polymers, they form a hydrogel that exhibits shear-thinning behavior during injection due to reversal of guest host bonds. Deploying GH hydrogels in cardiac tissues presents a challenge because the repetitive nature of the contractions causes repeated structural deformation to the gel, impacting the release of miRNAs, which in turn raises the risk of cardiomyopathy arising from excessive pro-proliferative signals to cardiomyocytes.

We also predicted that the cholesterol on the miR-302 mimics would interact with cyclodextrin such that the gel would erode at a different rate and that the interaction would alter the release of miRNA mimics negatively impacting the therapeutic effects. We discovered, however, that provided the amount of cyclodextrin is high enough, gel erosion is similar with and without cholesterol modification.

MicroRNAs

In one embodiment, a miR cluster is a genetic region or locus that contains a plurality of microRNAs. Exemplary microRNAs are disclosed in U.S. Published Application No. 2013/0035374, which is incorporated herein in its entirety and with respect to those sequences. In one embodiment, a miR cluster is a group of adjacent genes, which in one embodiment, are co-transcribed in a polycistronic manner. In one embodiment, the miR genes in a cluster are transcribed under the control of a single promoter. In another embodiment, a miR cluster is a group of adjacent and related genes. In one embodiment, a miR 302-367 cluster is a single sequence having multiple miRs, all corresponding to the 302-367 locus.

In another embodiment, the nucleic acid sequence is a homolog of the sequence described hereinabove. In one embodiment, the homolog is as described in PCT Patent Publication No: WO/2009/091659, which is incorporated by reference herein in its entirety, or another homolog known in the art.

In one embodiment, a microRNA (miR) 302-367 cluster comprises nine different miRNAs co-transcribed in a polycistronic manner: miR-302a, miR-302a*, miR-302b, miR-302b*, miR-302c, miR-302c*, miR-302d, miR-367 and miR-367*. In one embodiment, the nucleic acid sequence of miR-302b is: UAAGUGCUUCCAUGUUUUAGUAG (SEQ ID NO: 1; miRBase Accession No: MI0000772; ENTREZGENE: 442894; miRBase Accession No: MIMAT0000715). In one embodiment, the nucleic acid sequence of miR-302b* is: ACUUUAACAUGGAAGUGCUUUCU (SEQ ID NO: 2; miRBase Accession No: MIMAT0000714) optionally, the terminal U may be removed. In one embodiment, the nucleic acid sequence of miR-302c is: UAAGUGCUUCCAUGUUUCAGUGG (SEQ ID NO: 3; miRBase Accession No: MI0000773; ENTREZGENE: 442895; Accession No: MIMAT0000717); optionally, the 5' U may be removed. In one embodiment, the nucleic acid sequence of miR-302c* is: UUUAA-CAUGGGGGUACCUGCUG (SEQ ID NO: 4; miRBase Accession No: MIMAT0000716). In one embodiment, the nucleic acid sequence of miR-302a is: UAAGUGGUUC-CAUGUUUUGGUGA (SEQ ID NO: 5; miRBase Accession No: MI0000738; ENTREZGENE: 407028). In one embodiment, the nucleic acid sequence of miR-302a* is: UAAACGUGGAUGUACUUGCUUU (SEQ ID NO: 6; miRBase Accession No: MIMAT0000683). In one embodiment, the nucleic acid sequence of miR-302d is: UAAGUGCUUCCAUGUUUGAGUGU (SEQ ID NO: 7; miRBase Accession No: MI0000774; ENTREZGENE: 442896; Accession No MIMAT0000718). In one embodiment, the nucleic acid sequence of miR-367 is as follows AAUUGCACUUUAGCAAUGGUGA (SEQ ID NO: 8; miRBase Accession No: MIMAT0004686; ENTREZGENE: 442912). In one embodiment, the nucleic acid sequence of miR-367* is as follows ACUGUUGCUAAUAUGCAA-CUCU (SEQ ID NO: 9; miRBase Accession No: MI0000772).

Thus, in particular aspects, the guide and passenger molecules may be derived from the sequences below:

| Human miR | Sequence | SEQ ID NO |
|---|---|---|
| miR-302a | CCACCACUUAAACGUGGAUGUACUUGCUUUG AAACUAAAGAAGUAAGUGCUUCCAUGUUUUG GUGAUGG | 10 |
| miR-302b | GCUCCCUUCAACUUUAACAUGGAAGUGCUUU CUGUGACUUUAAAAGUAAGUGCUUCCAUGUU UUAGUAGGAGU | 11 |
| miR-302c | CCUUUGCUUUAACAUGGGGGUACCUGCUGUG UGAAACAAAAGUAAGUGCUUCCAUGUUUCAG UGGAGG | 12 |
| miR-302d | CCUCUACUUUAACAUGGAGGCACUUGCUGUG ACAUGACAAAAAUAAGUGCUUCCAUGUUUGA GUGUGG | 13 |

Unless stated otherwise, hydrogels were prepared with equimolar amounts of miR-302b and miR-302c, hereafter referred to collectively as miR-302 or an miR-302 mimic. The mimics contain cholesterol on the 5' end of the passenger strand. miR-302b and miR-302c are each typically present at around 200 µM to 250 µM, for example about 220 µM or about 210 µM, in the gel, to achieve the dosage amounts released.

Figure 7A:
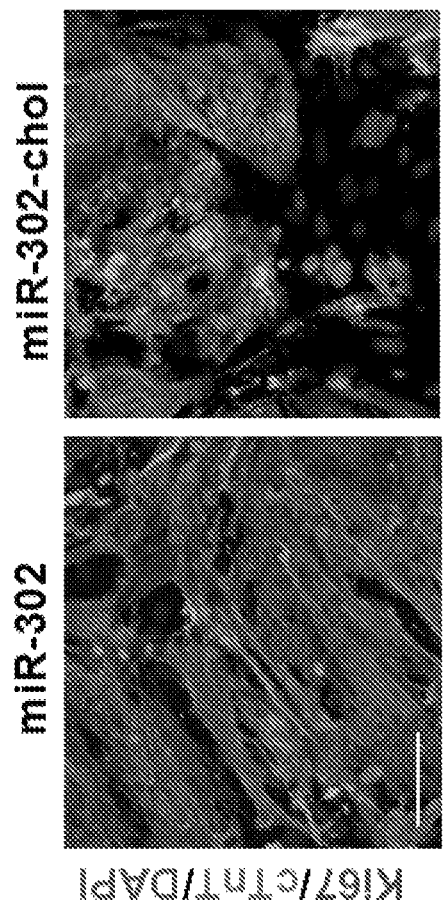
FIG. 7 Cholesterol-modification of miR-302 mimics Proliferation of neonatal mouse cardiomyocytes by un-modified (miR-302) and cholesterol modified (miR-302-chol) miR-302b/c mimics (200 µM), using FIG. 7A) co-staining and FIG. 7B) quantification of cardiac Troponin T and Ki67 to denote cardiomyocyte proliferation. Cardiomyocytes were treated with miR-302 for 24 hours; staining was performed after 48 hours. Scale bar=50 µm (mean±SD, n=3, $**p<0.01$).

Cholesterol-modified double-stranded RNAs are passively uptaken by cells in vitro and in vivo. We predicted, however, that the cholesterol would bind to the cyclodextrin, disrupting the interaction of the CD-HA and the AD-HA thus affecting the integrity of the GH hydrogel, in turn affecting the release profile of miR-302 mimics. To ensure that cholesterol modifications improved miR-302 mimic uptake, miR-302b and miR-302c with and without cholesterol modifications were added to mouse neonatal cardiomyocytes in culture and cells were stained with Ki67, a marker for proliferation. Cardiomyocytes treated with cholesterol-modified miR-302b and miR-302c mimics (miR-302-chol) were significantly more proliferative (Ki67$^+$) than those treated with unmodified mimics (FIG. 7).

Figure 1B:
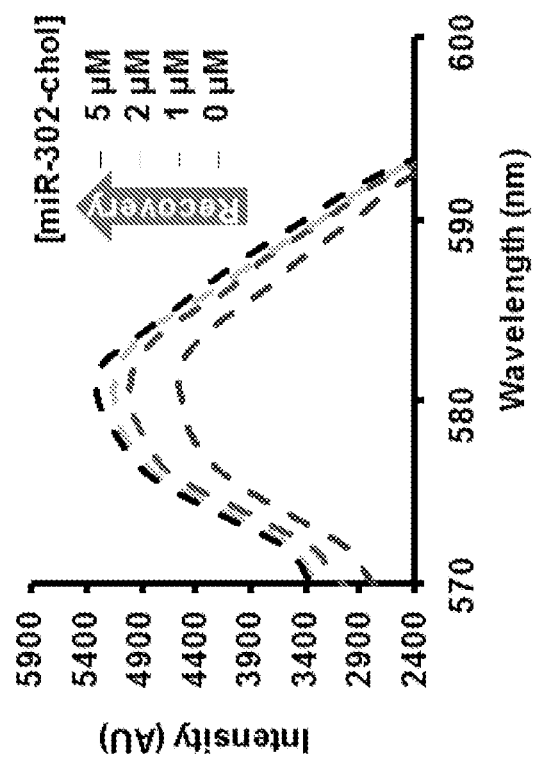
FIG. 1B. Rhodamine/CD-HA interactions lead to quenching of rhodamine fluorescence, but the fluorescence is recovered by titration of cholesterol-modified miR-302 into the system and displacement of rhodamine complexes, indicating complexation between cholesterol and CD.
Figure 8A:
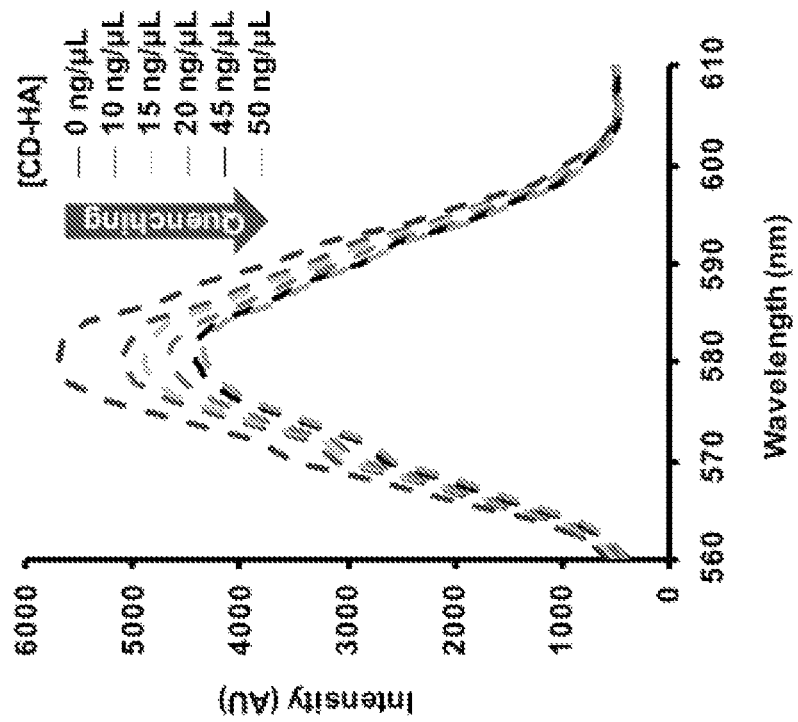
FIG. 8A Rhodamine fluorescence is quenched by CD-HA due to interactions of rhodamine and CD. Increasing amounts of CD-HA saturate quenching at 50 ng/µL.
Figure 8B:
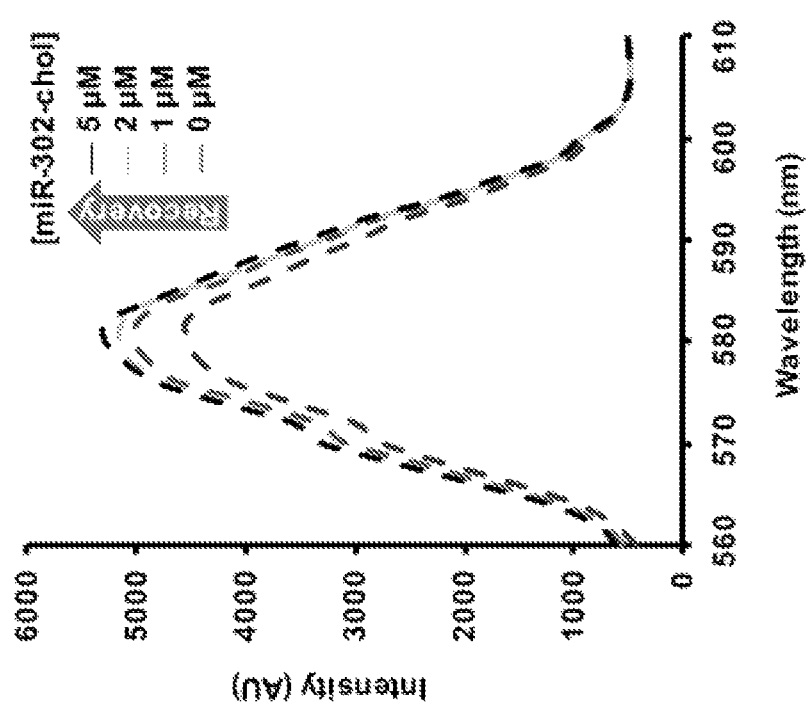
FIG. 8B. At a saturating dose of CD-HA (50 ng/µL), cholesterol-modified miR-302 interacts with CD-HA/Rho B to displace and unquench rhodamine, recovering fluorescence in a dose-dependent fashion.
Figure 8E:
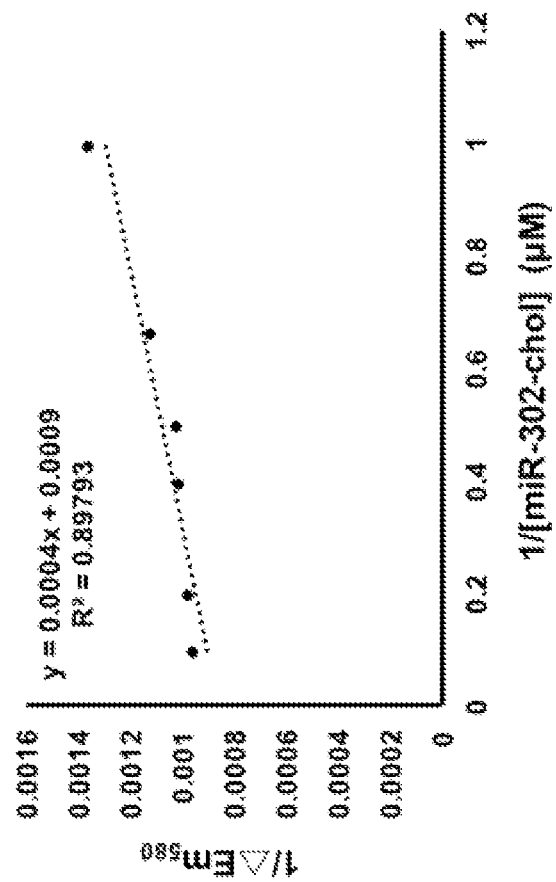
FIG. 8E. The Y-intercept of the best-fit line allows for the calculation of $\Delta Em_{580}max$, which was used to calculate the $K_a$ value from the slope $[1/(K_a*\Delta Em_{580}max)]$.

Due to lipophilicity interacts with CD as a host, suggesting that cholesterol-modified mimics may bind to CD-HA (FIG. 1A). To examine the effects of interaction on the gel, we developed a fluorometric binding assay to measure the interaction between cholesterol-modified miR-302 and CD-HA, based on similar assays. Rhodamine B (Rho) fluorescence was quenched by CD-HA due to guest-host interactions between CD and Rho; however, cholesterol has a higher affinity for CD and should displace Rho and recover fluorescence. We observed that cholesterol-modified miR-302 bound to CD-HA in a dose-dependent fashion, as added cholesterol-modified miR-302 increased solution fluorescence (FIG. 1B). In contrast, un-modified miR-302 did not change solution fluorescence (FIG. 8). Assuming negligible binding by Rho, a binding constant for miR-302-chol/CD-HA complex formation was approximated as $Ka=2.0\times10^3$ $M^{-1}$ by fitting to the Benesi-Hildebrand equation, which is in good agreement with the literature for cholesterol/CD complexes (FIG. 8).

Figure 9A:
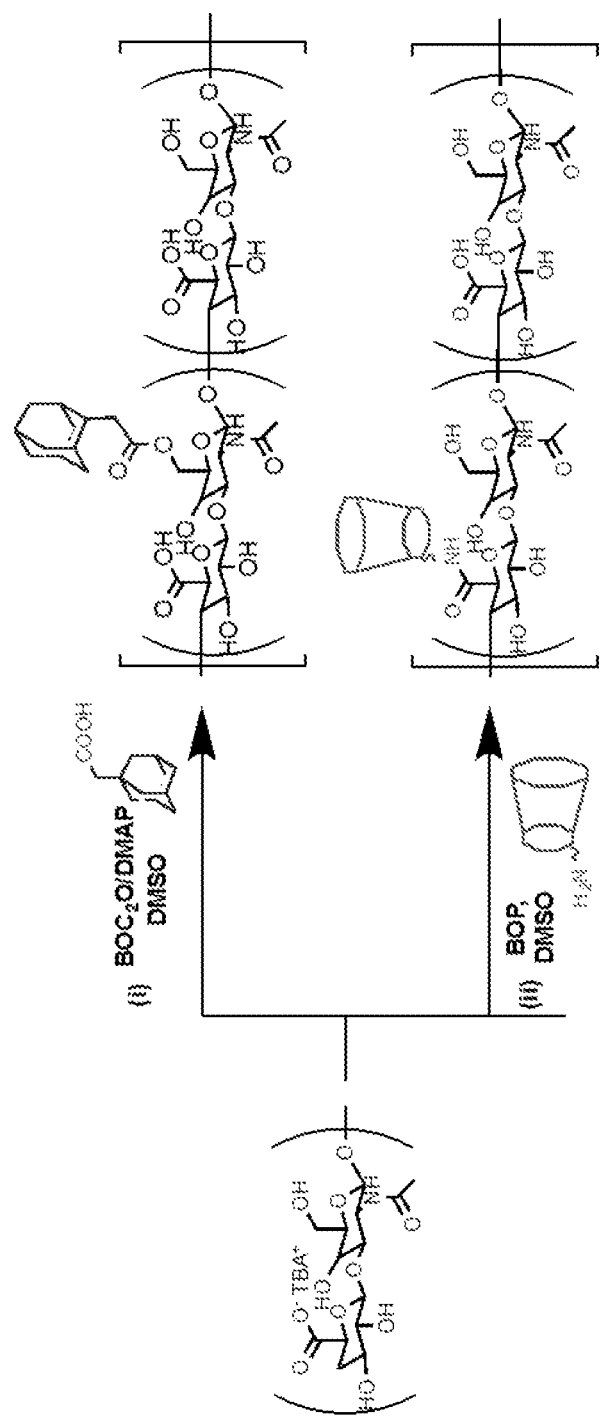
FIG. 9A AD-HA was synthesized from the esterification between 1-adamantaneacetic acid and the primary alcohol of HA by di-tert-butyl dicarbonate (Boc$_2$O).
Figure 9B:
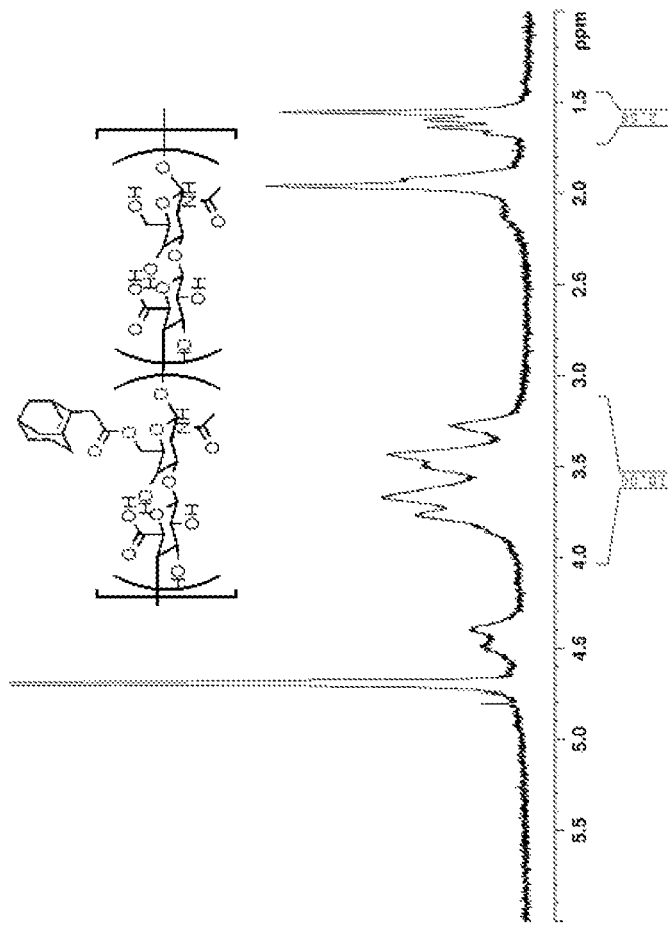
FIG. 9B. Adamantane functionalization was determined to be ~20% from integration of the ethyl multiplet of adamantane ($\delta=1.42-1.70$, 12 H) relative to the HA backbone ($\delta=3.10-4.10$, 10 H). CD-HA was synthesized from the amidation reaction between aminated cyclodextrin (mono-(6-Hexanediamine-6-deoxy)-β-cyclodextrin) and the carboxylic acid of HA by (benzotriazol-1-yloxy)tris(dimethylamino)phosphonium hexafluorophosphate.
Figure 9C:
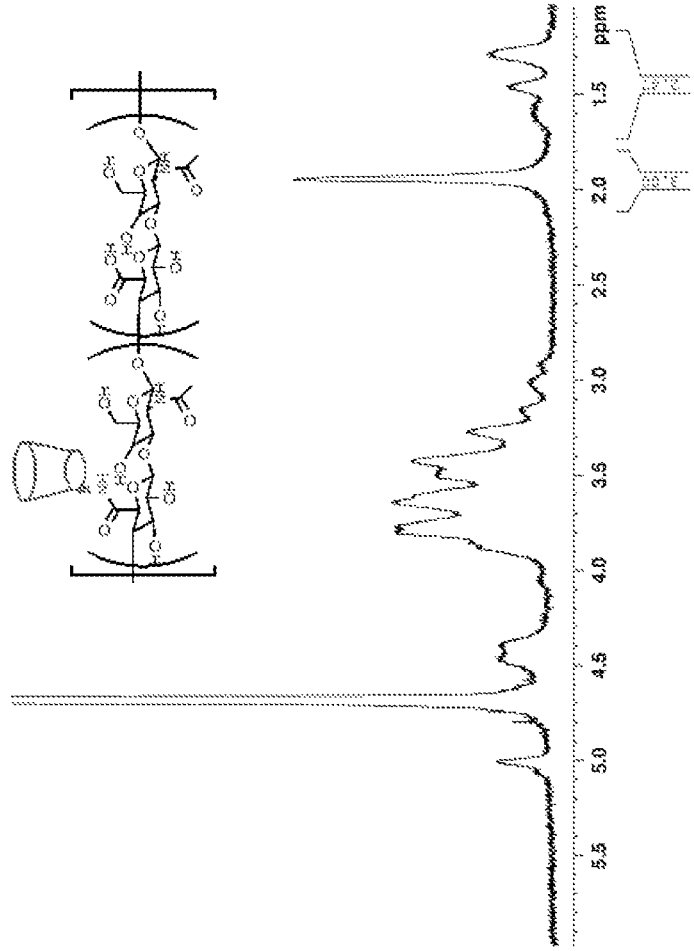
FIG. 9C. Cyclodextrin functionalization was determined to be ~20% by integration of the hexane linker (δ=1.22-1.77, 12 H) relative to the methyl singlet of HA (δ=2.1, 3 H)
Figure 10:
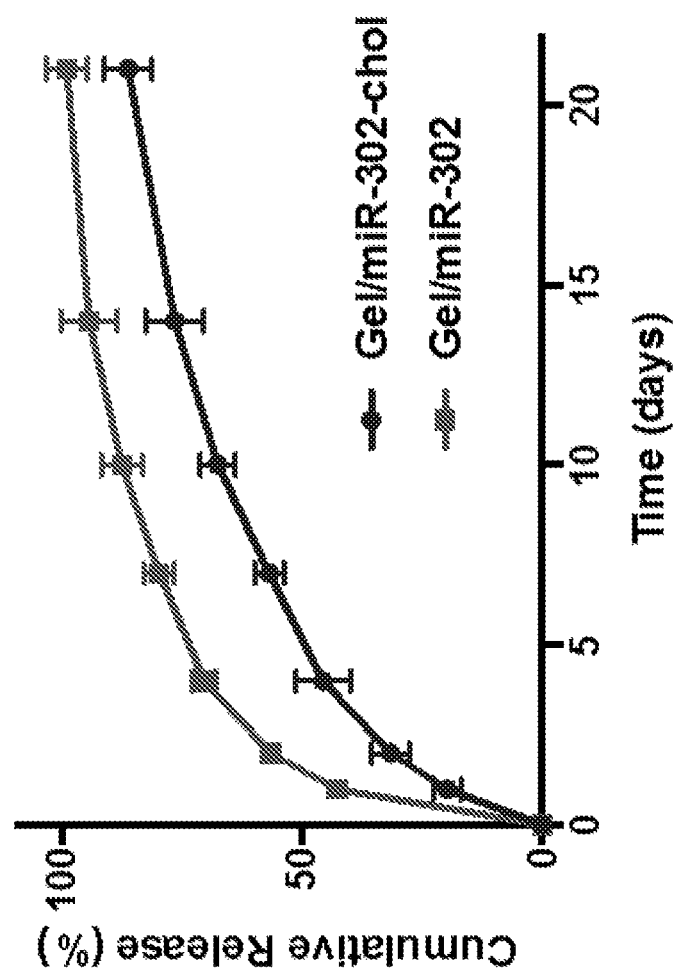
FIG. 10. Release of cholesterol-modified and un-modified miR-302. Gels (100 μL, 5 wt %) were assembled with either cholesterol-modified or unmodified miR-302 (210 μM of miR-302b and 210 μM of miR-302c). PBS was added above gels in microcentrifuge tubes and collected serially over three weeks to quantify total miR-302 release. At 21 days, gels were dissolved solution to determine the remaining miR-302 and all values were normalized to the cumulative miR-302. miR-302 release was slower when modified with cholesterol due to complexes between cholesterol and CD (mean±SD, n=3).

To assess the effect of cholesterol, cholesterol-modified miR-302 mimics were assembled into gels with CD-HA and AD-HA (~20% modification of HA with either CD or AD, FIG. 9.). Release of cholesterol-modified miR-302 was sustained from gels over three weeks (FIG. 1C), which was slower than the release of mimics without cholesterol (FIG. 10), confirming that cholesterol/CD interactions are complex and that the cholesterol modifies the miR-302 mimic release profile. Thus, the cholesterol-modified miRNA-302 gels disclosed herein provide for delayed release. In some aspects, the cumulative release is about 50% by about 5 days compared to above 60% for the non-cholesterol-modified miRNA control. See FIG. 10.

Figure 11A:
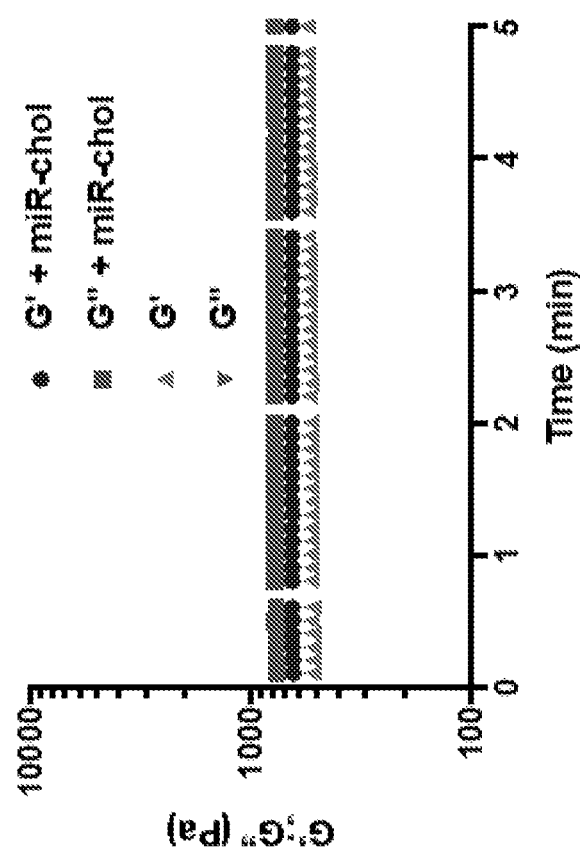
FIG. 11A. Time sweep of storage (G') and loss (G") moduli at 1 Hz, 0.5% strain of gels (5 wt %) alone or with encapsulated miR-302 (210 μM of miR-302b and 210 μM of miR-302c). miR-302 inclusion minimally affects moduli.
Figure 11B:
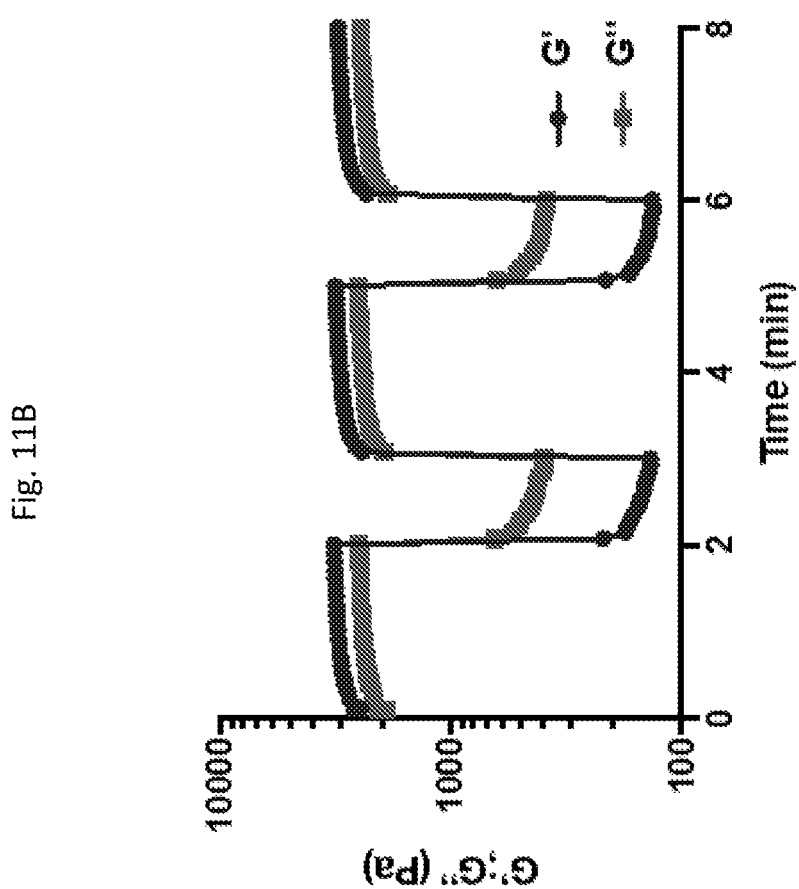
FIG. 11B Alternating low (0.5%) and high (250%, gray shading) strain at 20 Hz demonstrating shear-thinning and rapid recovery of hydrogel with miR-302. G' declines below G" in response to high strain, indicating flow and more liquid behavior at high strains. Upon cessation of strain, G' and G" both rapidly recover to initial mechanics.
Figure 12A:
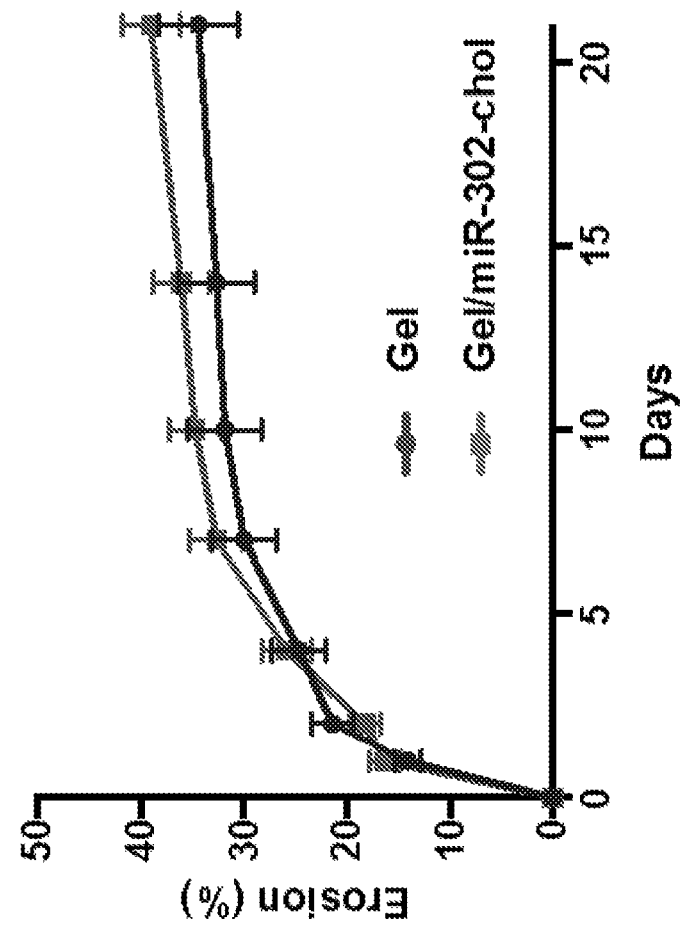
FIG. 12A shows a time course.
Figure 12B:
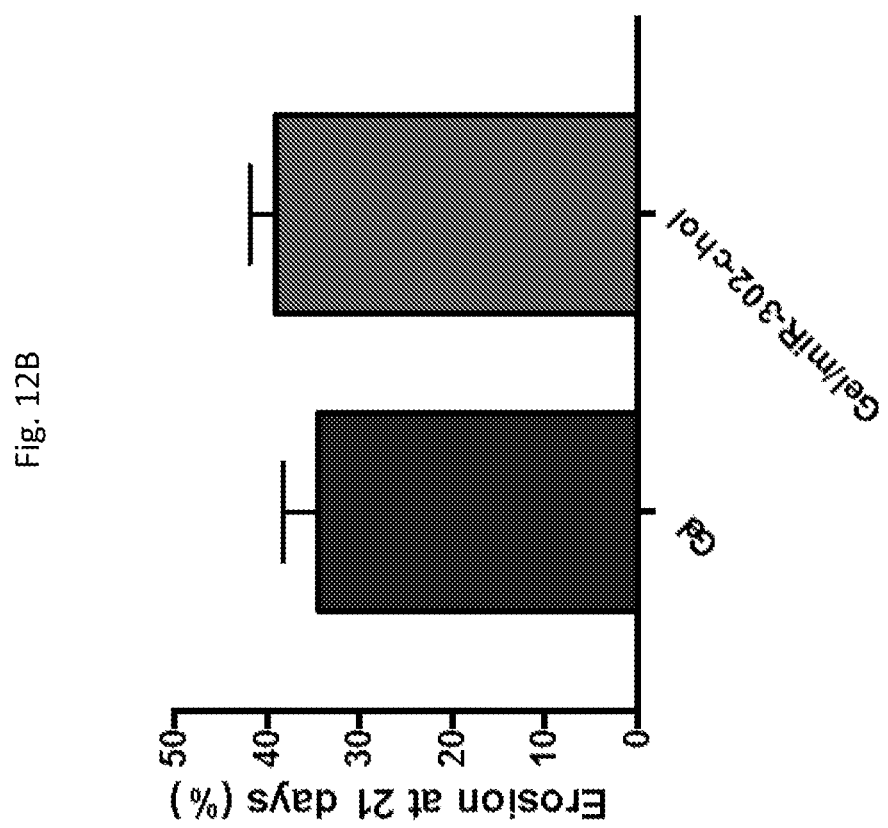
FIG. 12B provides a comparison.

We also investigated various physical properties of the gels with cholesterol-modified mimics. To confirm that cholesterol-modified miR-302 did not affect mechanical and erosion behavior of gels, we performed oscillatory rheology and gel erosions assays with and without encapsulated miR-302. Storage (G') and loss (G") moduli were equivalent for gels with and without encapsulated cholesterol-modified miR-302 (FIG. 11A). Shear-yielding and recovery were also observed in response to alternating high and low strain, demonstrating the ability of these gels to thin under shear strain and rapidly reassemble upon cessation of strain, permitting injection and rapid recovery of the gel/miR-302 system (FIG. 11B). Gel erosion was not affected by inclusion of cholesterol-modified miR-302 in the system, using a uronic acid assay to measure HA release (FIG. 12). Thus, we have provided gels comprising cholesterol-modified miR-302 mimics that provide enhanced cellular uptake and improved affinity for the gel without compromising gel mechanics, shear-thinning, or erosion.

Figure 4A:
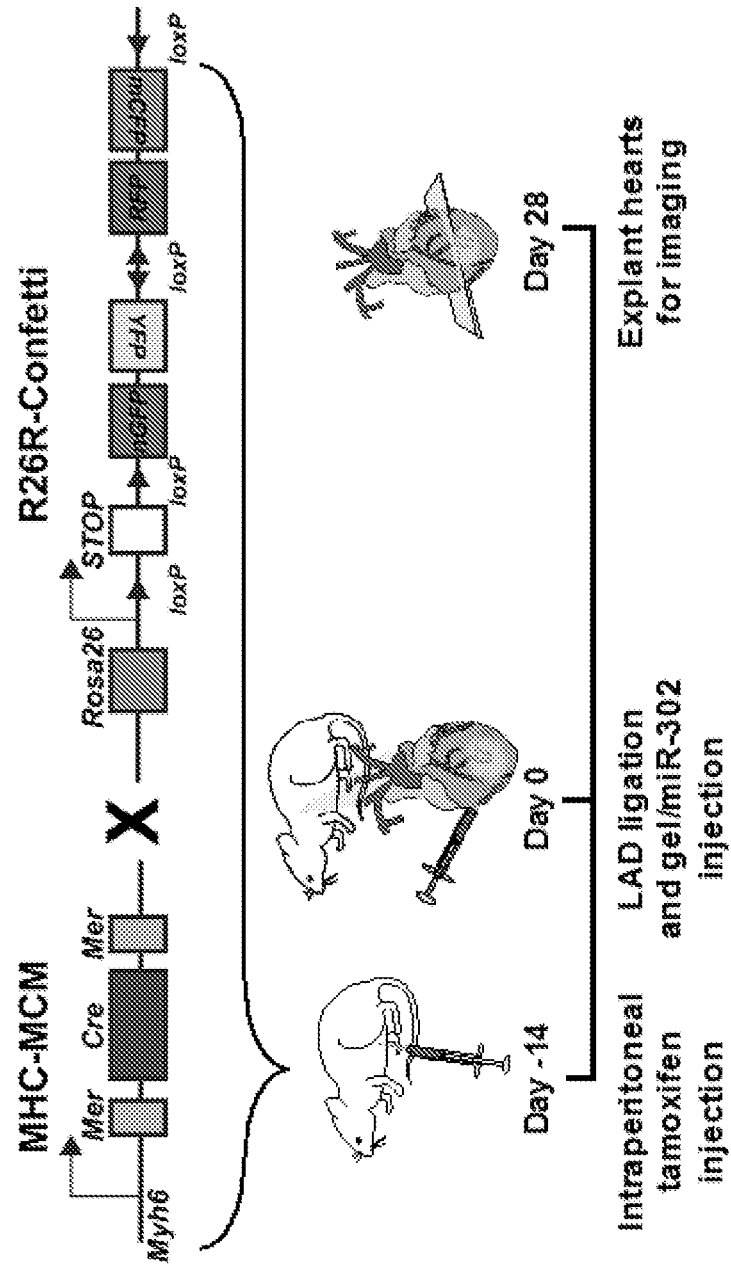
FIG. 4A. Schematic representation of lineage-tracing strategy and experimental design. To trace clonal proliferation, mice were cross-bred with Myh6$^{MerCreMer}$ and R26R$^{Confetti}$. The expression of Myh6 leads to Cre-loxP recombination with consequent random activation of one of four fluorescent reporter proteins (nGFP, YFP, RFP and mCFP) with each color representing a different clone from a Myh6 positive cardiomyocyte. In our experimental design, mice were injected with tamoxifen intraperitoneally to induce the stochastic expression of nGFP, RFP, YFP and mCFP. After 14 days, the LAD was ligated to induce ischemic injury and gels were injected in the border zone of the infarct downstream. At 28 days, hearts were collected for analysis of clonal expansion.
Figure 4C:
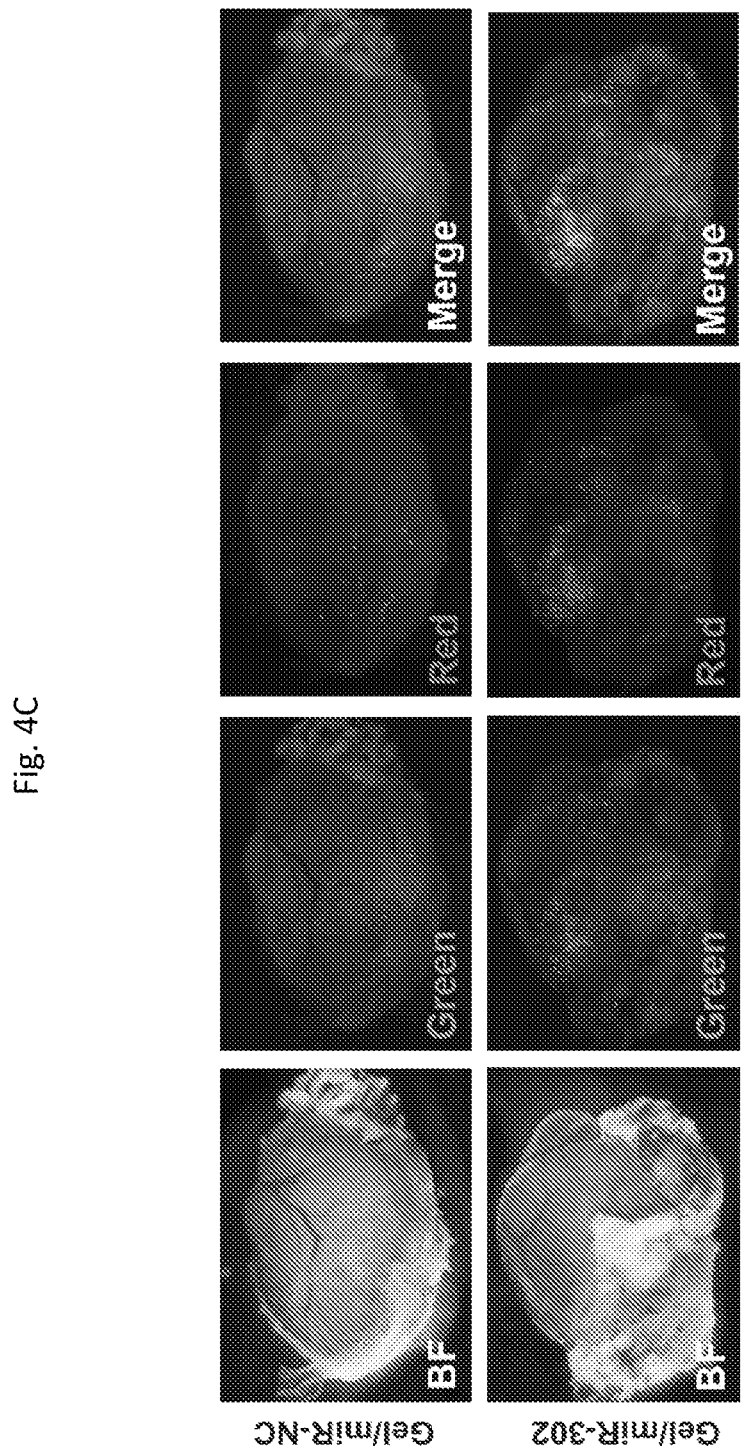
FIG. 4C. Fluorescent scans of gross heart specimens immediately after explanting at 28 days. Fluorescence is displayed in the green and red channels to indicate labeling of cardiomyocytes in both gel/miR-NC and gel/miR-302 treated groups. Presence of increased fluorescence in both channels of the gel/miR-302 treated groups demonstrates clonal expansion.
Figure 5A:
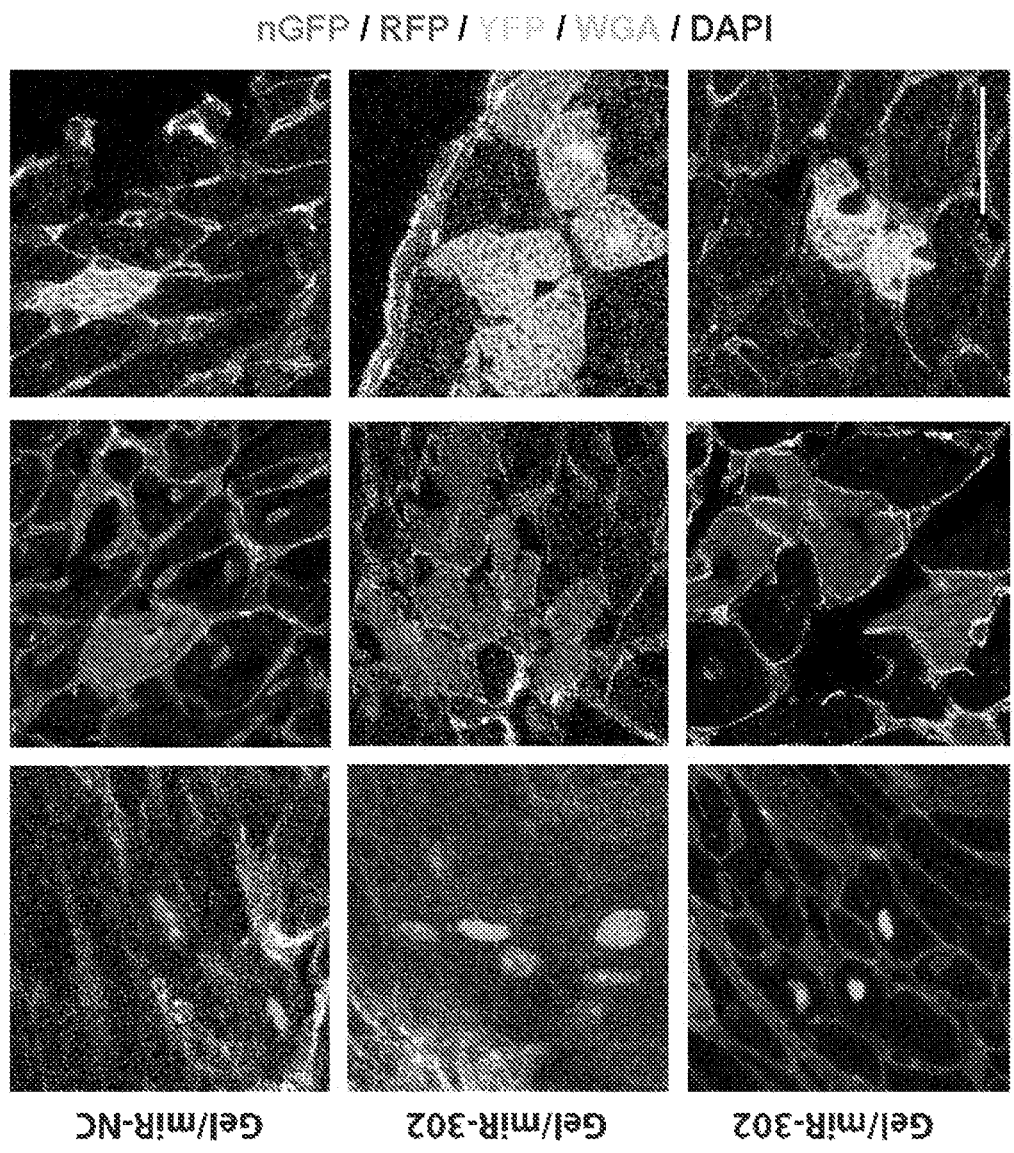
FIG. 5A. Representative sections from confocal imaging with labeled cardiomyocytes expressing nGFP, RFP, or YFP. Gel/miR-NC sections consisted mostly of individual cardiomyocytes that were spatially separated. In gel/miR-302 treated groups, multiple clones were observed in all three fluorescent in channels in close proximity, consisting of several daughter cells from a single parent cell. WGA separates individual cardiomyocytes and permits identification of clones, specifically to differentiate multiple cardiomyocytes from multi-nucleated cardiomyocytes. Scale bar=50 µm.
Figure 5B:
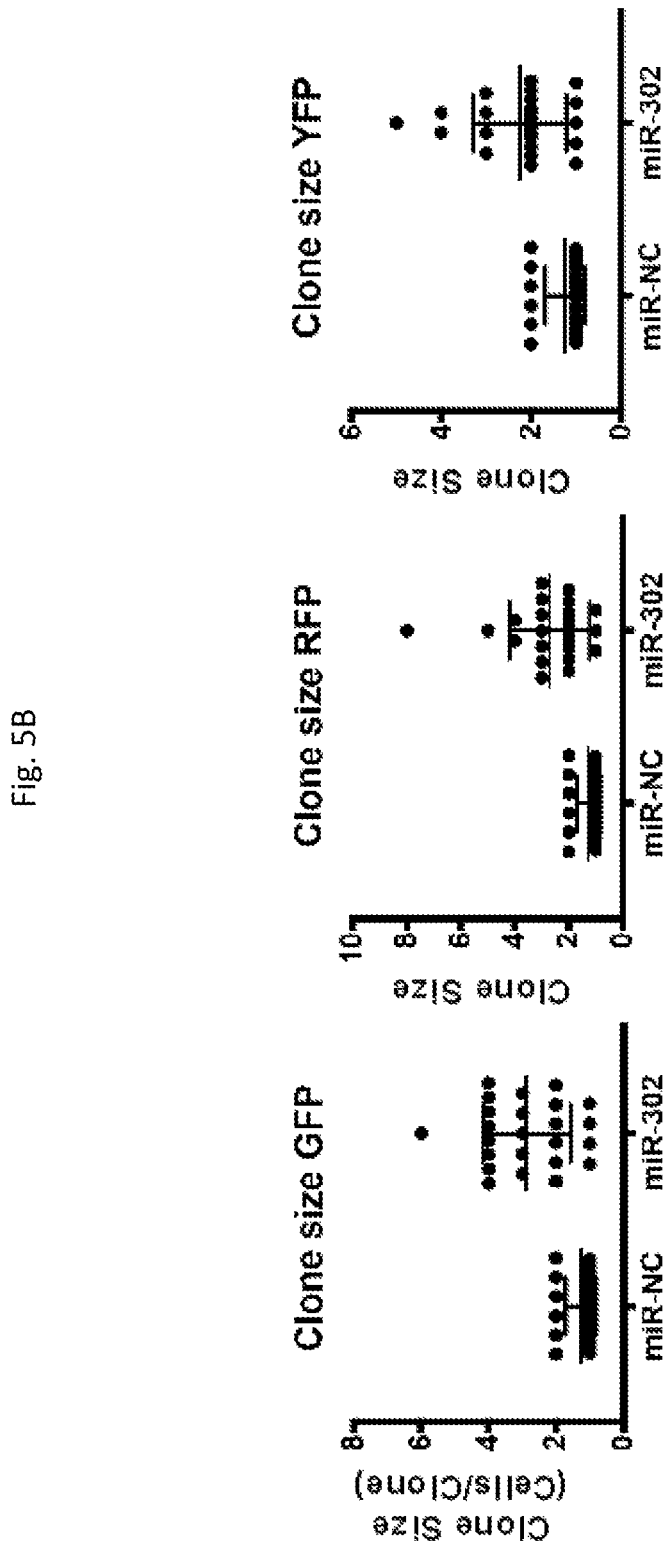
FIG. 5B. Quantification of cells to a clone in the nGFP, RFP, and YFP channels. Clones are identified as cells within 50 µm proximity to one another. Clones consisting of one cell are not technically clones but stochastically labeled single cells, but are still counted as part of the analysis to demonstrate they are the ubiquitous in the gel/miR-NC groups.

The hydrogels disclosed herein induce clonal proliferation. To verify that the proliferation observed in the gel/miR-302 treated animals could generate additional new cardiomyocytes after ischemic injury, we performed clonal lineage tracing analysis using a multicolor R26R-Confetti Cre-reporter system which allows tracing cell lineage by expression of fluorescent proteins (FIG. 4; FIG. 16). Clonal cardiomyocytes expressing nGFP, RFP, and YFP were clearly identified in miR302-injected hearts whereas few clones were observed with control miRNA injection. Among labeled cardiomyocytes, multiple clusters expressing nGFP were detected in gel/miR-302 injected hearts and localized to the border zone of the infarction. The average distance between nGFP cells was significantly lower in gel/miR-302 treated groups, suggesting that these cells were derived from a common single cell. Further analysis with Wheat Germ Agglutinin (WGA) staining to identify cell membranes showed fluorescent cells within 50 μm were mostly contiguous in gel/miR-302 treated groups but not in gel/miR-NC groups (FIG. 5a). In gel/miR-NC groups, distant cells (>50 μm) were often interspersed by unlabeled cardiomyocytes. Using 50 μm as a standard, we quantified the number of cells per single clone for nGFP, RFP, and YFP across all sections of the heart in the border zone of infarcts. Gel/miR302-injected hearts had a significant increase in the number of cells per clone (as many as 8) to suggest that these cells were derived from a common parent cell that had divided (FIG. 5b). Thus the hydrogels disclosed herein induce clonogenic cardiomyocyte proliferation.

Native miR connect nucleotides via phosphodiester bond and the miR disclosed herein may connect nucleotides via phosphodiester bonds. In other aspects, however, one or more phosphodiester bonds may be replaced by a different type of chemical bond. For example, one or more bonds may be a phosphorothioate bond. In another example, embodiments, one or more of the nucleotides may have a p-ethoxy linkage. Decreasing phosphodiester bonds and increasing phosphorothioate bonds will enhance nuclease resistance, promoting biological effect. Due to the structural requirements of microRNAs, however, not all the bonds will be changed. In certain aspects, the passenger strand contains more modifications than the guide strand. In certain other aspects, the microRNA is a locked nucleic acid (LNA). Additional description for modifications is described in Baumann, V, and J Winkler. "miRNA-Based Therapies: Strategies and Delivery Platforms for Oligonucleotide and Non-Oligonucleotide Agents." Future medicinal chemistry 6.17 (2014): 1967-1984. PMC. Web. 24 Mar. 2018., which is incorporated for all purpose and in particular the suitable modifications.).

In particular aspects, the release profile for releasing microRNA from the hydrogel deliver a transient dose within a particular time after being applied to the cardiomyocytes. In particular aspects, the hydrogel delivers at least 80% of the dose within 21 days, at least 85% of the dose within 21 days, at least 90% of the dose within 21 days, or at least 95% of the dose within 21 days. In certain particular aspects the transient release may be over a period shorter than 21 days; for example, at least 85% of the dose may be released by 7 days, by 10 days, or by 14 days. Thus, in particular aspects, the hydrogels transiently deliver the effective dose over a period of up to 21 days.

Enhanced Proliferation in Adult Cardiac Tissue Ameliorates MI Impact

In particular aspects, the hydrogels used herein are applied to adult heart cardiomyocytes. The adult heart is a terminally differentiated organ and the ability to stimulate cardiomyocyte proliferation is thus particularly desirable. The hydrogels disclosed herein provide robust and sustained proliferation at five days in the adult heart.

In certain embodiments, enhanced cardiomyocyte proliferation may be determined by measuring increased expression of markers of cardiac proliferation. Exemplary markers include Ki67, PH3, Aurora B Kinase (AURKB), a marker for cytokinesis. The gels disclosed herein provided improved cardiomyocyte proliferation with as many as ~6%, ~2% and ~1% of cells in fields surrounding injection sites (within 200 microns) staining positive for Ki67, PH3 and AURKB, respectively. In contrast, injections without miR-302 mimics led to very low levels (<1%) of Ki67, PH3 and AURKB, corroborating previous reports of the very rare and limited capacity for adult cardiomyocyte self-renewal.

The hydrogels disclosed herein provide enhanced cardiac function after myocardial infarction (MI). Cardiac function can be analyzed through echocardiography and measurements of left ventricular end diastolic volume (LVEDV), left ventricular end systolic volume (LVESV), ejection fraction (EF), and fractional shortening (FS) were made. LVEDV and LVESV are markers of ventricular volume at the beginning and end of a cardiac cycle, respectively, while ejection fraction and fractional shortening measure the efficiency of cardiac function. Left ventricular internal diameters during systole (LVIDS) and diastole (LVIDD) may be obtained from 2D M-mode imaging, where fractional shortening was calculated per the equation EF=[(LVIDD-LVIDS)/LVIDD].

Ejection fraction measures the change in cardiac volume during a cardiac cycle (LVEDV-LVESV) normalized to the amount at the beginning of the cycle (LVEDV) and is a volumetric measure of cardiac function. Left ventricular end systolic volume (LVESV) and left ventricular end diastolic volume (LVEDV) was obtained from B-mode imaging by manually tracing the left ventricular endocardial border. Ejection fraction was calculated per the equation EF=[(LVEDV-LVESV)/LVEDV].

The hydrogels disclosed herein restore LVEDV to the same levels as found in non-infarcted subjects. LVEDV in gel/miR-302 was decreased compared to gel/miR-NC. Whereas LVEDV in both sham (PBS) and control (gel/miR-NC) treated mice were increased compared to non-infarcted mice, LVEDV from gel/miR-302 groups were unchanged compared to non-infarcted mice.

LVESV demonstrated similar results. Here, LVESV of gel/miR-302 mice were lower than LVESV of both sham and control groups. LVESV of PBS and gel/miR-NC treated mice were higher than that of non-MI mice. However, LVESV of gel/miR-302 mice was not different from that of non-infarcted mice. From a functional perspective, whereas PBS and gel/miR-NC treated animals had significantly reduced EF and FS, EF and FS of gel/miR-302 treated animals were not significantly different from non-infarcted mice Thus, the hydrogels disclosed herein provide lowered LVEDV and LVESV levels compared to controls and not statistically different from volumes in non-infarcted mice. This data shows that gels improves cardiac volumes while preventing ventricular dilation and pathologic remodeling.

Additional measures of cardiac function provide further evidence of these beneficial effects. Gel/miR-302 treated mice had reduced cardiac remodeling, demonstrated by reductions in LVEDV and LVESV, measures of cardiac volumes at the beginning and end of a single contraction, respectively, compared to PBS or gel/miR-NC controls LVEDV and LVESV of gel/miR-302 treated animals were not significantly different from non-infarcted mice.

Fractional shortening is a 1D measurement of cardiac function that measures change in straight line distance between the anterior and posterior left ventricular wall at the beginning and during a cardiac cycle. Our analysis of FS followed a similar trend. Fractional shortening was higher in gel/miR-302 treated mice compared to gel/miR-NC. Further, whereas PBS and gel/miR-NC treated mice had lower FS than that of non-infarcted mice, FS of gel/miR-302 treated mice was not different from that of non-infarcted mice.

Our data supports a mechanism by which hydrogels induces cardiomyocyte proliferation in adult cardiac tissue in as little as five days after injection. As established by the Confetti model of infarction, at around 4 weeks, cardiomyocyte proliferation manifests in the form of increased clones of cardiomyocytes in the border zone of infarction. As a result of the increased cardiomyocytes demonstrable decreases in LVEDV and LVESV are obtained, supporting improved ventricular dilation and remodeling. Similarly, the increased EF and FS support enhanced cardiac contractility and function by administering the hydrogelgel/miR-302 disclosed herein. Thus, gel/miR-302 injection can decrease cardiac end diastolic volume, by about 30% to about 45% (39%) and systolic volumes about 45 to about 55% and improve ejection fraction about 25% to about 35% (e.g., about 32%) and fractional shortening was improved by about 60% to about 70% (e.g., about 64%) by four weeks compared to controls.

Taken together, this improvement in both EF and FS not only supports the improved cardiac volumes but also demonstrates that hydrogels disclosed herein promote significant improvement in cardiac function following MI. Further, the data suggest that the local improvement in cardiomyocyte proliferation and cell number plays a potentially major role in limiting infarct expansion, minimizing wall stress, and improving cardiac contractility.

Routes of Administration

The hydrogels are typically administered by injection into the cardiac muscle. In aspects, the injection is proximal to the left anterior descending (LAD) artery. In particular aspects, the Injections were made inferolateral to the proximal left anterior descending (LAD) artery.

The device used to perform the injection is a syringe having sufficient flow to permit passage of the gel. In some aspects, the syringe may be a 27-Gx½" U-100 insulin syringe. In other aspects, delivery may be percutaneous, such as via a catheter.

EXAMPLES

Example 1

Preparation and Loading Guest-Host Hydrogel

Material Synthesis: Sodium hyaluronate (LifeCore, Chaska, MN) was converted to a tetrabutylammonium salt (HA-TB A) by exchange against Dowex-100 resin and neutralization by tetrabutylammonium hydroxide. CD-HA and AD-HA were synthesized as previously described. Briefly, CD-HA was prepared by amidation between 6-(6-aminohexyl)amino-6-deoxy-β-cyclodextrin and HA-TBA in the presence of benzotriazol-1-yloxy) tris(dimethylamino) pho sphoniumhexafluoropho sphate (BOP). AD-HA was synthesized by esterification of HA-TBA with 1-adamantane acetic acid in di-tert-butyl bicarbonate ($BOC_2O$) and 4-dimethylaminopyridine (DMAP). Products were dialyzed, frozen and lyophilized prior to use. $^1H$ NMR (Bruker) at 360MHz was used to determine final product modification, which was approximately 25% of HA disaccharide repeats for both CD-HA and AD-HA.

miRNA molecules used had the following sequences:

```
cel-miR-67 (miR-NC)
                              (Guide; SEQ ID NO: 14)
5'-CGCUCAUUCUGCCGGUUGUUAUG-3'

(Passenger; SEQ ID NO: 15)
3'-AGAUGAGAAAGAUCCUCCAACACU-Chol-5' mmu-miR-302b (miR-302b)
                              (Guide; SEQ ID NO: 16)
5'-ACUUUAACAUGGGAAUGCUUUCU-3'

(Passenger; SEQ ID NO: 17)
3'-GAUGAUUUUGUACCUUCGUGAAU-Chol-5'
```

-continued mmu-miR-302c (miR-302c)

(Guide; SEQ ID NO: 18)
5'-GCUUUAACAUGGGGUUACCUGC-3'

(Passenger; SEQ ID NO: 19)
3'-GGUGACUUUGUACCUUCGUGAA-Chol-5'

Example 2

Rhodamine Quenching Assay

To further examine the interaction between cholesterol and CD, we developed a fluorometric binding assay to measure the interaction between cholesterol-modified miR302b/c and CD-HA. This assay is based on the ability for cholesterol to bind to and displace Rhodamine B from β-cyclodextrin, leading to unquenching and increased fluorescence. Gels were prepared as described in Example 1. Rhodamine B (50 ng/μL) was mixed with varying amounts of CD-HA (0-50 ng/μL) towards a final concentration of 200 μL in DI H2O to determine saturating concentrations for quenching. For unquenching assays, Rhodamine B (50 ng/μL) was mixed with miR-302 mimics (0-5 μM) in a final volume of 200 μL. Emission was measured from 530 to 580 nm on a Tecan Infinite200 plate reader at an excitation of 550 nm. miR-302b-chol affinity for Rho/CD-HA complexes was calculated by fit to the Benesi-Hildebrand equation.

Figure 1C:
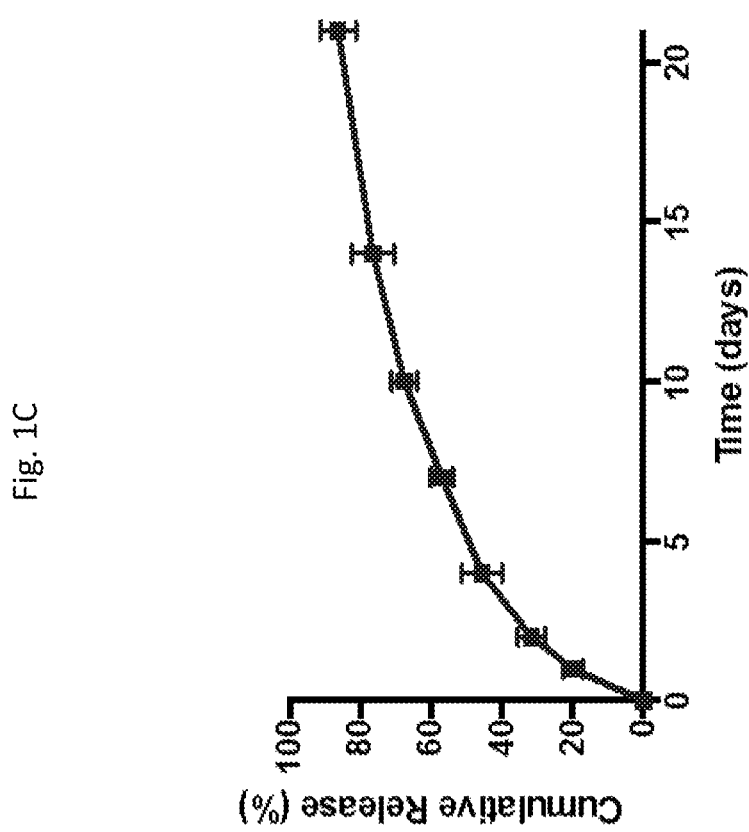
FIG. 1C. Release of cholesterol-modified miR-302b and miR-302c (210 µM of each) from gels (5 wt %) over three weeks quantified by RiboGreen, a commercially available RNA quantification kit (mean±SD, n=3).

We found that cholesterol-modified miR-302 mimics bound to CD-HA in a dose-dependent fashion (FIG. 1B). Assuming the contribution of Rhodamine is negligible, a binding constant for miR-302-chol/CD-HA complex formation can be approximated as $Ka=2.0\times10^3$ $M^{-1}$ by fitting to the Benesi-Hildebrand equation. In support of this interaction, cholesterol-modified miR-302b and miR-302c mimics were assembled into gels with CD-HA and AD-HA (FIG. 1C). Release of miR-302b/c was sustained from gels over three weeks, leading to decreased overall release at all timepoints compared to unmodified mimics, which were more rapidly released (FIG. 1D). Thus, cholesterol modification increased the complexity of miR-302b/c release through affinity to CD-HA.

Example 3

Rheological Characterization

To confirm that cholesterol-modified miR-302b and miR-302c mimics, hereafter termed miR-302, did not affect mechanical and erosive behaviors of hydrogels, we performed oscillatory rheology and hydrogel erosions assays.

Measurements were performed using an AR2000 stress-controlled rheometer (TA Instruments) fitted with a 20 mm diameter cone and plate geometry, 59 min 42 s cone angle, and 27 μm gap. Rheological properties were examined by time sweeps (1.0 Hz; 0.5% strain). For shear recovery experiments, shear-thinning was performed at 250% strain with recovery at 0.5% strain, each at 20 Hz.

Gel erosion at two weeks was also not affected by inclusion of miR-302 in the system from a uronic acid assay measuring total hyaluronic acid degradation (FIG. 1E).

Example 4 miR-302 Release and Bioactivity

CD-HA and AD-HA polymers are sterilized under UV irradiation in our cell culture hood for 1 hour. To make 100 uL gels, the dry polymers are each resuspended in 20 uL of miR-302b and 20 uL of miR-302c each at 525 uM (dissolved in DI water). 10 uL of PBS are added to CD-HA and AD-HA so the final volume of CD-HA and AD-HA is 50 uL (20 uL miR-302b, 20 uL of miR-302c, 10 uL of PBS). Then, gels are mixed by injecting the two components between two insulin syringes multiple times before centrifuging at max speed to get rid of air bubblesPolymer/miRNA solutions were mixed manually and centrifuged.

Gels were incubated with OPTI-MEM in 1.5 mL Eppendorf tubes with supernatants collected and replaced at D1, D4, D7, D10, D14 and D21. Total miRNA concentration in releasates was quantified by RiboGreen® according to manufacturer's protocols (Thermo Fisher Scientific). Briefly, 20 μL of releasate was incubated with Hi-Range RiboGreen Buffer and fluorescence was measured at excitation of 500 nm and emission of 520 nm on a Tecan Infinite microplate reader.

Neonatal Cardiomyocyte Isolation and Culture: Ventricular cardiomyocytes from neonatal mice were isolated as described previously. Eulalio, A. et al. Functional screening identifies miRNAs inducing cardiac regeneration. *Nature* 492, 376-81 (2012). Briefly, ventricles from neonatal mice (postnatal day 0-3) were separated from atria, cut into pieces and then subjected to trypsin (0.5%) digestion buffer in calcium free HBSS containing 10 mM HEPES and 0.54 mM EDTA under constant stirring. After digestion for 18 hours at 4° C., minced hearts were dissociated with calcium free HBSS supplemented with 10% horse serum, 5% FBS, and 10mM HEPES. Cells were then washed with calcium free DMEM supplemented with 10% horse serum and 5% FBS. After a final wash, the cells were plated on uncoated plastic dishes for 2 hours with medium supplemented with 10% horse serum and 5% FBS. Non-attached cells were passed through a cell strainer (70 uM, BD Falcon) and seeded on a gelatin coated 96-well plate at the density of 15,000 cells/well. After incubation for 48 hours, the majority of cells started to beat. Mouse ventricular cardiomyocytes prepared using this procedure consistently yielded a purity of >90%. For proliferation assays, gel/miR-302 releasates or controls were added to cells in 96-well plates for 24 hours.

At 48 hours, cells were fixed with 4% paraformaldehyde for 15 min, permeabilized with 0.5% Triton X-100 in phosphate buffered saline (PBS) solution for 10 min, followed by 30 min blocking in 5% Donkey Serum (Jackson ImmunoResearch). Cells were then stained overnight at 4° C. with Troponin T (Thermo Scientific) and Ki-67 (Abcam) primary antibodies diluted in blocking solution and then secondary antibodies conjugated to Alex Fluor-488 and 555. Images were acquired with Leica TCS SP8 scope. Cell counting was performed in triplicates from ten representative fields per sample.

Figure 2A:
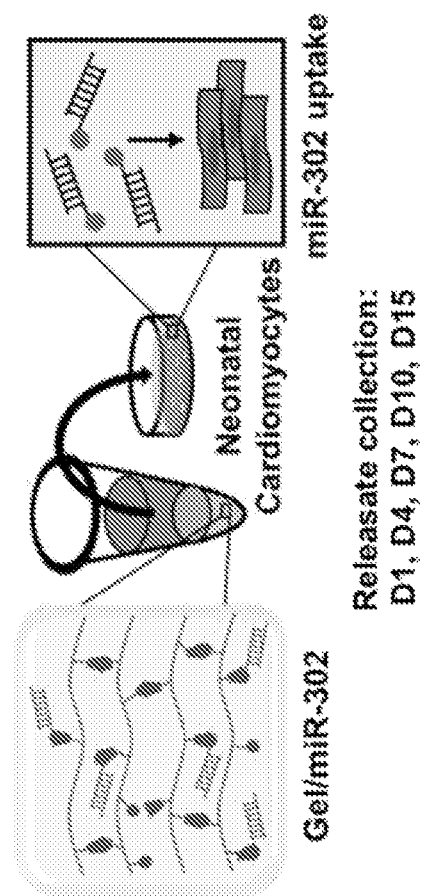
FIG. 2A. Schematic of miR-302 supernatant collection and cardiomyocyte uptake. Gel/miR-302 (100 µL) assemblies were formed in microcentrifuge tubes with cholesterol-modified miR-302 (210 µM of miR302b and miR302c) or miR-NC. OPTI-MEM (500 µL) was added above gels and supernatant was collected, frozen, and replaced at D1, D4, D7, D10 and D15. Supernatants collected from each timepoint were added to primary neonatal cardiomyocytes in culture for 24 hours. At 48 hours, cardiomyocytes were stained for Ki67, cardiac Troponin T, and DAPI to detect proliferation.
Figure 2B:
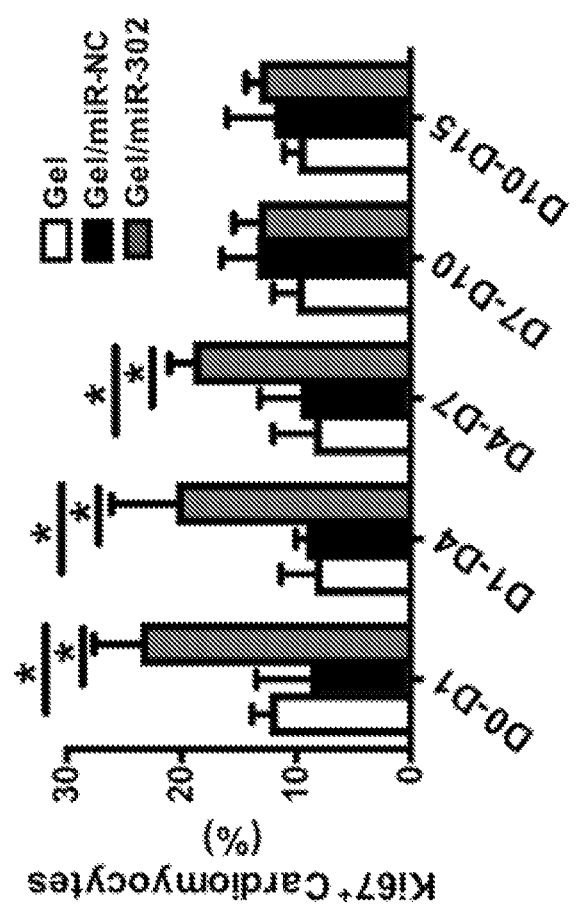
FIG. 2B Quantification of Ki67 positive, Troponin T positive proliferation of neonatal cardiomyocytes from gel supernatants from D0-D1, D1-D4, D4-D7, D7-D10 and D10-D15 in vitro cultures demonstrating proliferative effects from early gel/miR-302 release out to 7 days (mean±SD, n=3 per condition, *p<0.05).
Figure 2C:
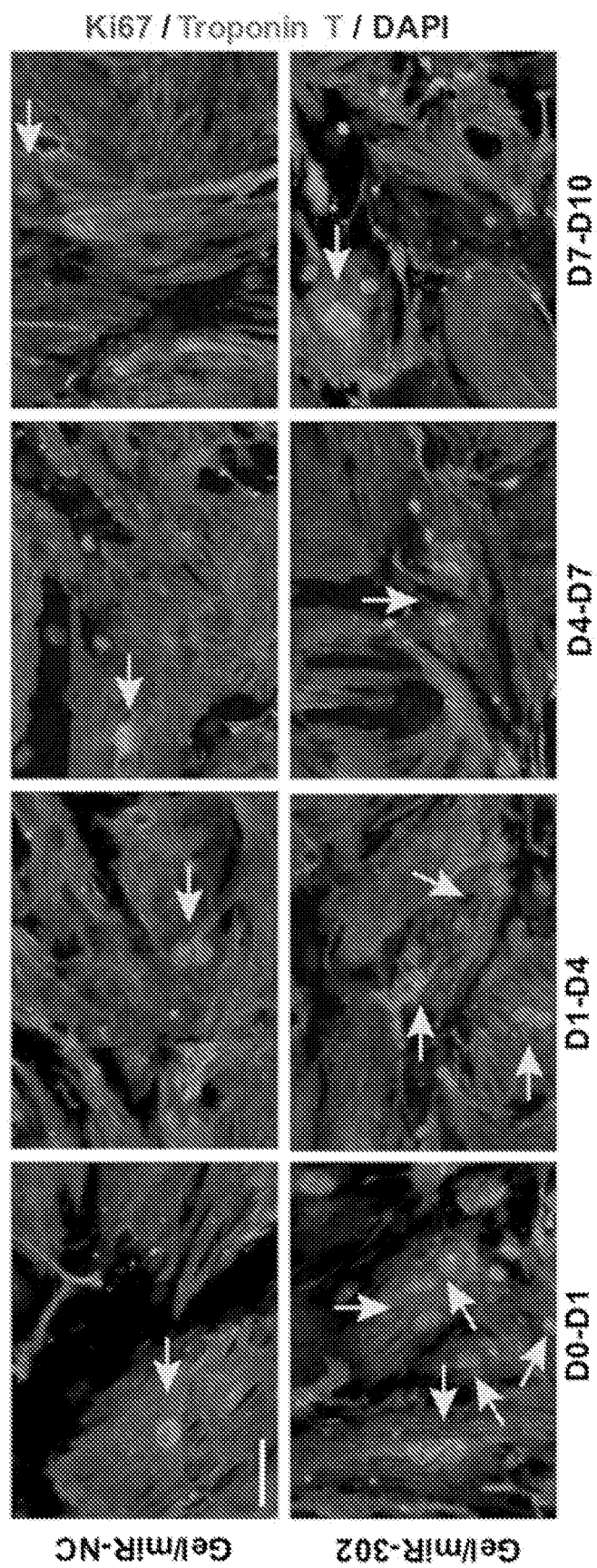
FIG. 2C. Representative images of Ki67 positive, troponin T positive neonatal cardiomyocytes (yellow arrows) to demonstrate increased Ki67 staining up to 7 days for gel/miR-302. Scale bar: 50 µm.

To assess cardiomyocyte proliferation from gel/miR-302 assemblies in vitro, OPTI-MEM supernatants from gel assemblies with miR-302 (releasates) were collected and replaced serially over two weeks (FIG. 2A). Neonatal cardiomyocytes were treated with releasates from gel/miR-302 assemblies or controls. Gel/miR-302 assemblies significantly enhanced neonatal mouse cardiomyocyte proliferation from D0-D1, D1-D4 and D4-D7 compared to gel/miR-NC or gel alone (FIG. 2B and FIG. 2C). During these timepoints, approximately 25% of total cardiomyocytes (cTnT+) stained Ki67 positive in gel/miR-302 treatment groups compared to <15% in control groups.

This significant enhancement in cardiomyocyte proliferation can be attributed to sustained release of miR-302 from gels over one week. At later timepoints D7-D10, D10-D14, D14-D21, there was no difference in cardiomyocyte proliferation between gel/miR-302 and controls. This is most likely attributed to decreased absolute miR-302 concentration released during these intervals. miRNA mimics may also be partially degraded at these later timepoints due to extended length of release, leading to diminished bioactivity.

Taken together, the gels disclosed herein enhance neonatal cardiomyocyte proliferation in vitro over one week. Notably, the gel release profile shows that the dosage obtained from one administration is similar to repeated serial dosaging over a week.

Example 5

In vivo Proliferation Measurement

Prior to use, polymers were sterilized under UV irradiation for 1 hour. Gels were formed with siRNAs as previously described and manually transferred to a 27-G×½" U-100 tuberculin syringe (Terumo) under sterile conditions on ice. Male C57BL/6 mice were randomized to receive 10 μL total of gel or control injection (2×5 μL). Mice were anesthetized with 3% isoflurane in an induction chamber (2 L) and endotracheally intubated (Harvard Apparatus Regenerative Technology) with 1% isoflurane. A left lateral thoracotomy was performed at the fourth intercostal space to expose the heart. Injections were made inferolateral to the proximal LAD without infarct. Following injection, the chest was closed in 3 layers with a 3-0 polypropylene suture and animals were allowed to recover. After 5 days, the heart was excised, briefly washed in PBS, weighed, fixed in 4% PFA, embedded in paraffin and further processed for immunofluorescence. Slides were washed in TBS with 0.05% Triton X-100 (TBST) and blocked in 10% goat serum followed by incubation with primary antibodies against: Cardiac Troponin T (Thermo Scientific), Ki-67 (Abcam), Histone H3 phosphorylated at serine10 (Cell Signaling), Aurora B kinase (Sigma), or Yap (Cell Signaling). After 24 hours, sections were incubated with secondary antibodies conjugated to Alex Fluor-488, 555 or 647 (Life Technologies). Nuclei were identified by counter-staining sections with DAPI (Vector Labs). Slides were then mounted in Vectashield. A series of confocal images (z-stack) were acquired either by Leica STED Super-Resolution Microscope or LSM 710 Zeiss. Images were analyzed and constructed by ImageJ software and Imaris. Cells were counted by two independent investigators from a minimum of three representative sections of both injection sites per mouse.

Myocardial Infarction Model: Male C57BL/6 mice were randomized to receive 10 μL total of gel or control injection (2×5 μL). Mice were anesthetized with 3% isoflurane in an induction chamber (2 L) and endotracheally intubated (Harvard Apparatus Regenerative Technology) with 1% isoflurane. A left lateral thoracotomy was performed at the fourth intercostal space to expose the heart. The LAD was ligated 2 mm below the left auricle and infarction was visualized from blanching of the left ventricle. Injections were made lateral to the infarct. The chest was closed in 3 layers with a 3-0 polypropylene suture and animals were monitored during recovery for signs of stroke or embolization.

Transthoracic Echocardiography: Mice were anesthetized with 3% isoflurane induction following maintenance at 2% by nose cone. Hair was removed using Nair and limbs were taped onto the metal EKG leads. Echo was performed using a VisualSonic Vevo 2100 system with a 40-MHz transducer for cardiac imaging. The transducer was placed parallel along the long axis of the left ventricle for a long axis view or rotated clockwise for short axis view. Images were analyzed using Vevo200 1.6 VisualSonic software. All measurements were measured across a minimum of five cardiac cycles. Left ventricular infernal diameters during systole (LVIDS) and diastole (LVIDD) were obtained from 2D M-mode imaging, where fractional shortening was calculated per the equation EF=[(LVIDD−LVIDS)/LVIDD]. Left ventricular end systolic volume (LVESV) and left ventricular end diastolic volume (LVEDV) was obtained from B-mode imaging by manually tracing the left ventricular endocardial border. Ejection fraction was calculated per the equation EF=[(LVEDV−LVESV)/LVEDV].

Example 6

Effect of Cholesterol Modification in Neonatal vs Adult Cardiomyocytes

Neonatal cardiomyocytes display greater regenerative capacity than adult cardiomyocytes. To confirm we could restore cardiac function in adult cells, we first confirmed that the hydrogel could regenerate neonatal cardiomyocytes.

In Vitro Bioactivity of gel/miR-302 Assemblies

To assess cardiomyocyte proliferation from gel/miR-302 assemblies in vitro, supernatants from gel assemblies with miR-302 were collected and replaced serially over two weeks (FIG. 2a). Neonatal mouse cardiomyocytes were treated with supernatants from gel/miR-302 or controls and stained with Ki67, cardiac Troponin T, and DAPI. Gel/miR-302 assemblies significantly enhanced neonatal mouse cardiomyocyte proliferation (~20-25% positive for Troponin T and Ki67) from D0-D1, D1-D4 and D4-D7 compared to gels with a non-specific sequence (gel/miR-NC) or gels alone (-10% positive for Troponin T and Ki67) (FIG. 2b,c). The significant enhancement in cardiomyocyte proliferation can be attributed to sustained release of miR-302 from gels for up to one week. At later times (D7-D10, D10-D14, D14-D21), there was no difference in cardiomyocyte proliferation between gel/miR-302 and controls, due to low, non-active levels or potential miRNA degradation over long release times. Since our previous study showed that transient delivery of miR-302 for one week could enhance cardiac function in vivo, the gel release profile in vitro suggests that gel/miR-302 may replicate serial dosing for one week from a single gel injection.

In Vivo Bioactivity of gel/miR-302 after Cardiac Injection

Figure 3A:
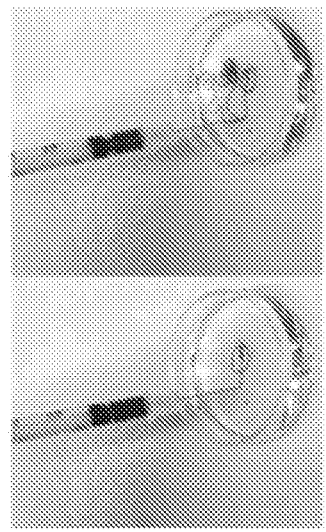
FIG. 3A Pre-formed gel (5 wt %, blue dye) injected from a 27Gx½" syringe into water, to demonstrate rapid reassembly and minimal dispersion of cargo upon injection.
Figure 3B:
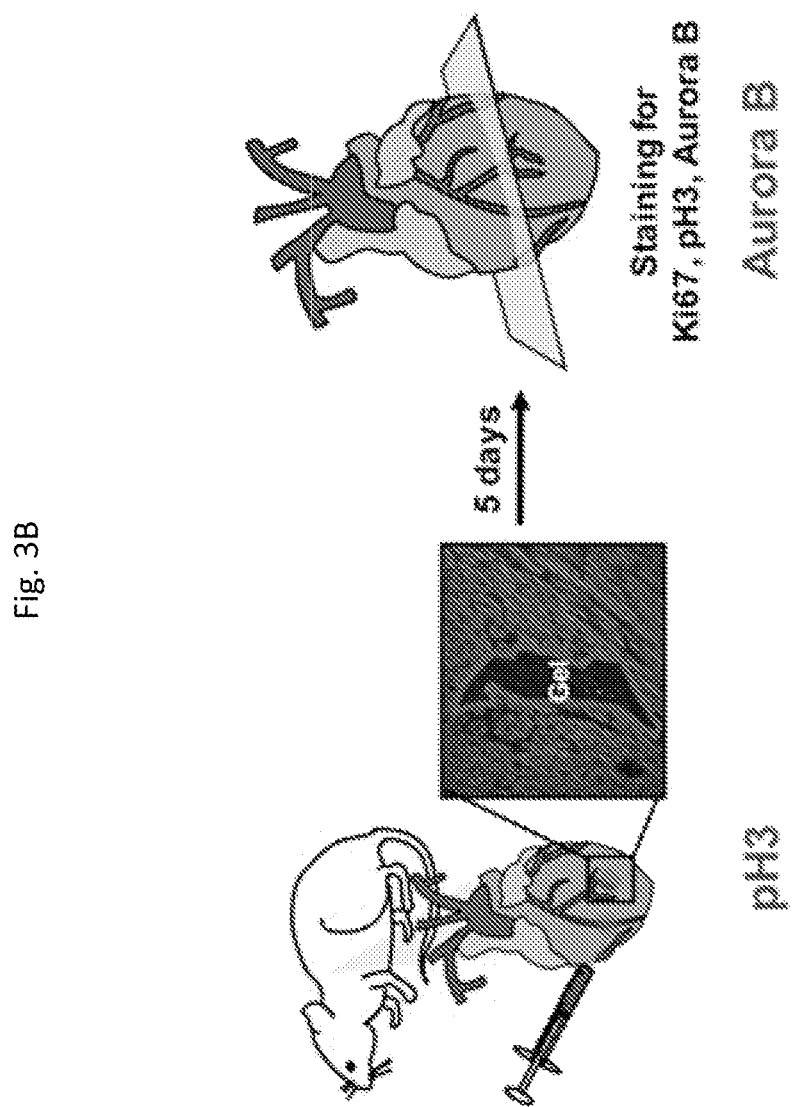
FIG. 3B Schematic for intramyocardial gel injections into non-infarcted murine hearts. Two injections were made inferolateral to the proximal LAD below the left atrial appendage in non-infarcted mouse hearts after thoracotomy. At five days, hearts were sectioned and stained for Troponin T and Ki67, pH3 or Aurora B.

Neonatal cardiomyocytes retain some proliferative capacity and therefore may be more responsive to miR-302 stimulation; thus, we sought to test the bioactivity of gel/miR-302 assemblies in adult cardiomyocytes, which have extremely limited capacity to proliferate both in vitro and in vivo. Gels were ejected from 27G×½" tuberculin syringes into water to demonstrate their capacity for injection with rapid reassembly and minimal cargo loss observed (FIG. 3a). Gels were then injected in two regions (5 μL per site) inferior and lateral to the proximal left anterior descending artery (LAD) in non-infarcted hearts of adult male mice, which corresponds to the left and right border zone of a left ventricular infarct (FIG. 3b). At five days, hearts were explanted, sectioned and stained for markers of cardiac proliferation (Ki67, pH3) and cytokinesis (Aurora B Kinase). Sites of injection or needle tracts were identified from Troponin T negative areas and proliferation in cardiomyocytes (Troponin T positive) was quantified around these sites of injection for all three markers.

Figure 3C:
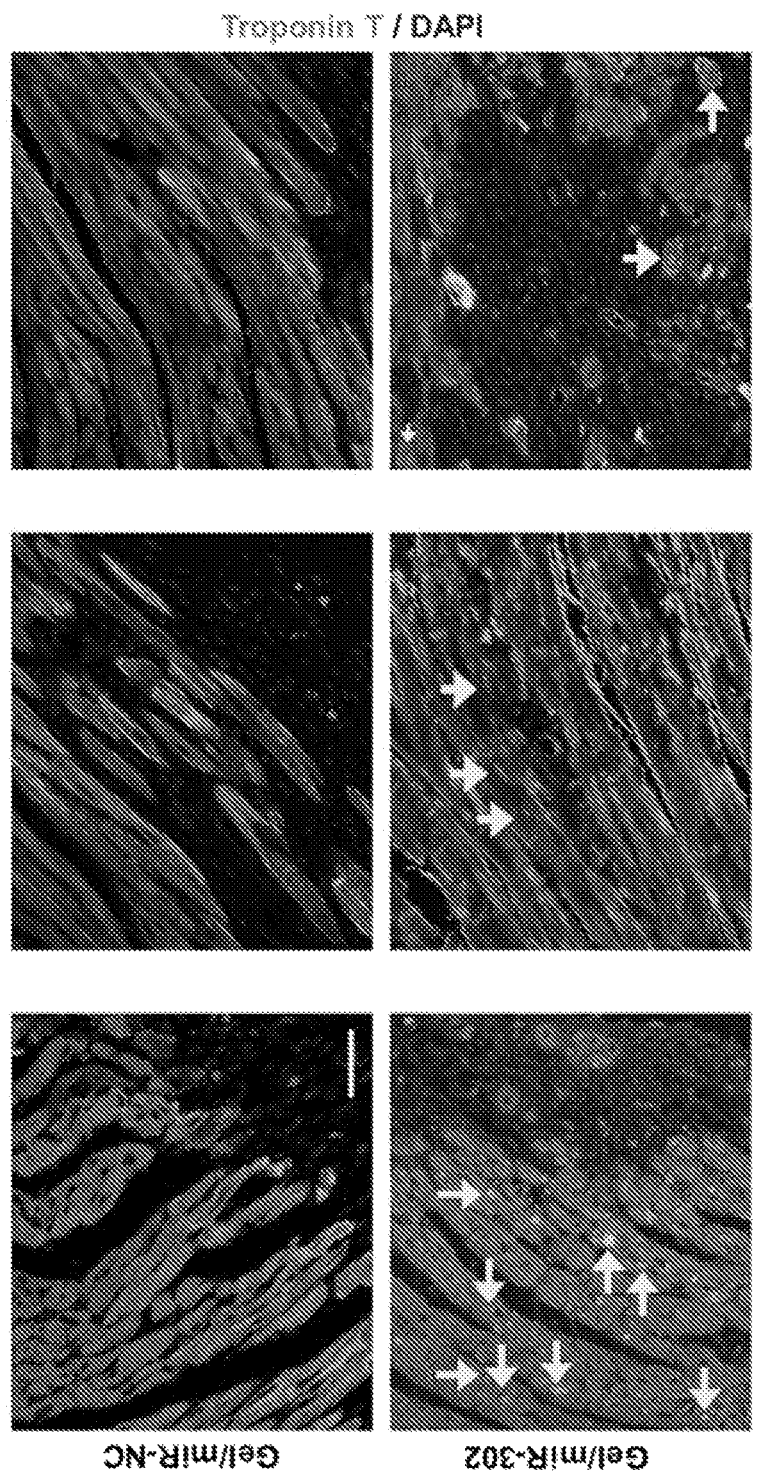
FIG. 3C Ki67, pH3 and Aurora B positive cardiomyocytes (yellow arrows) surrounding injection sites at low magnification to demonstrate increased proliferation from all three markers in gel/miR-302 treated groups. Scale bar=50 µM. d, e, f) High magnification views of Ki67, pH3, and Aurora B positive cardiomyocytes surrounding gel/miR-302 injection sites with quantification to show increased proliferation in gel/miR-302 treated groups. Scale bar=5 µm (mean±SD, n=3 animals per group, $*p<0.05$ $**p<0.01$). With respect to all figures, all data are reported as means±standard deviation (SD) and performed in triplicates unless otherwise indicated. For in vivo studies, there was a minimum of three mice per group unless otherwise indicated. Comparisons between two groups were performed by Students t-test with two-tailed criteria and significance determined at $p<0.05$. For comparison between multiple groups, significance was determined by one-way ANOVA with post hoc testing. Bonferroni correction was used to account for multiple comparisons, with $\alpha=0.05$.
Figure 3D:
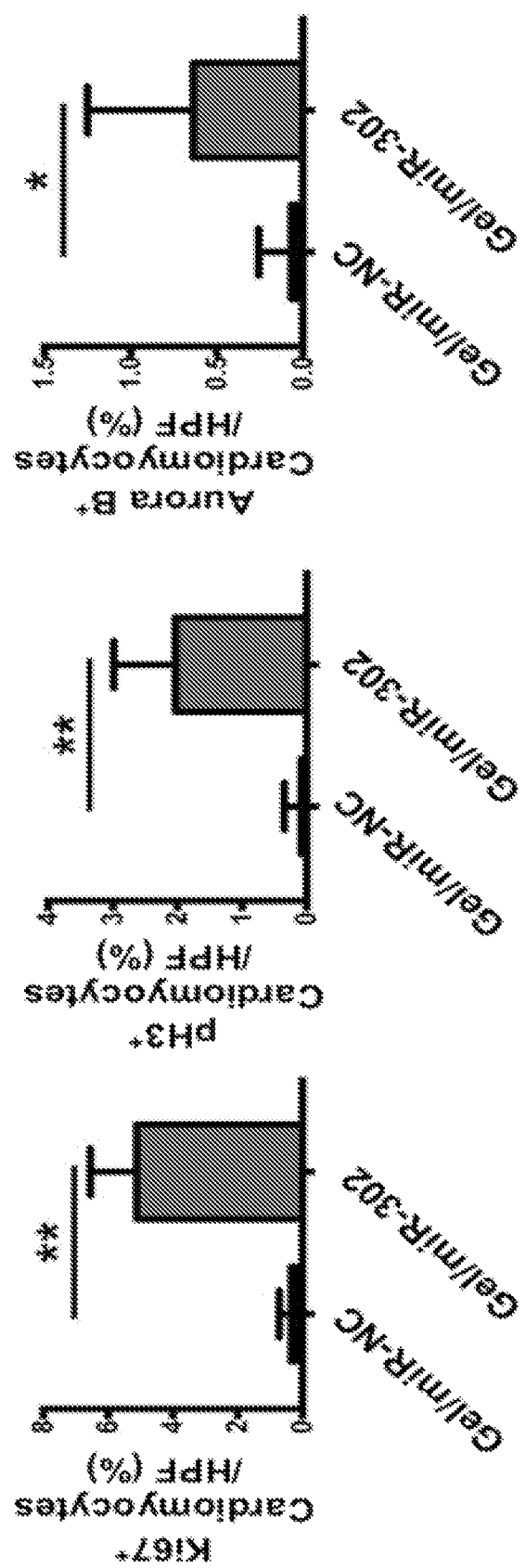
FIG. 3. In vivo cardiomyocyte proliferation.
Figure 13:
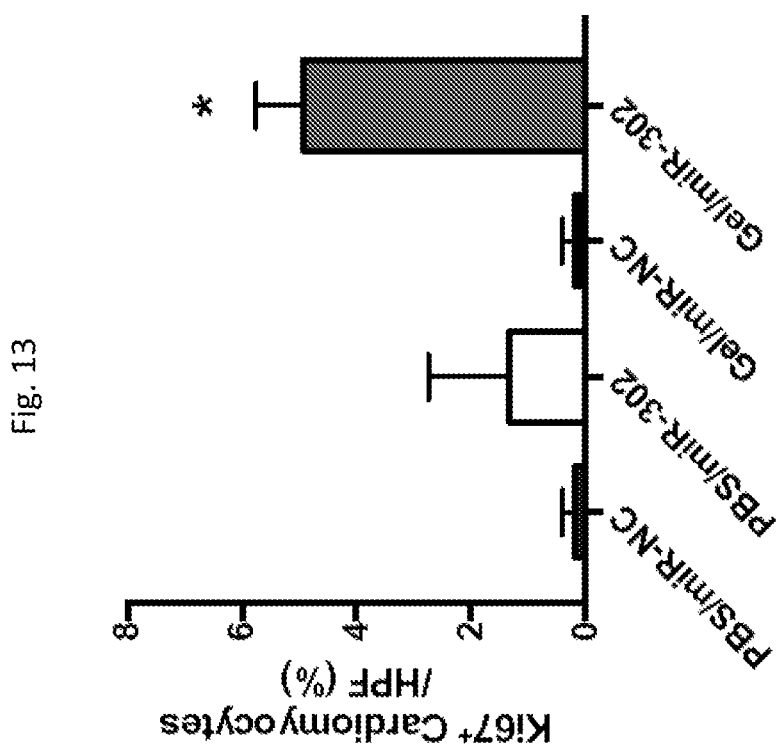
FIG. 13. Comparison of gel and PBS injections of miR-NC and miR-302. Mice were randomized to receive miR-302 or miR-NC 2×5 μL injections with gel or PBS in non-infarcted heart tissue inferior and lateral to the LAD at the left atrial appendage. At five days, hearts were sectioned and stained for Ki67. Quantification of Ki67 in HPFs surrounding both injection sites for a minimum of three mice per group (mean±SD, n=3 animals per group, *p<0.05 compared to all groups).
Figure 14A:
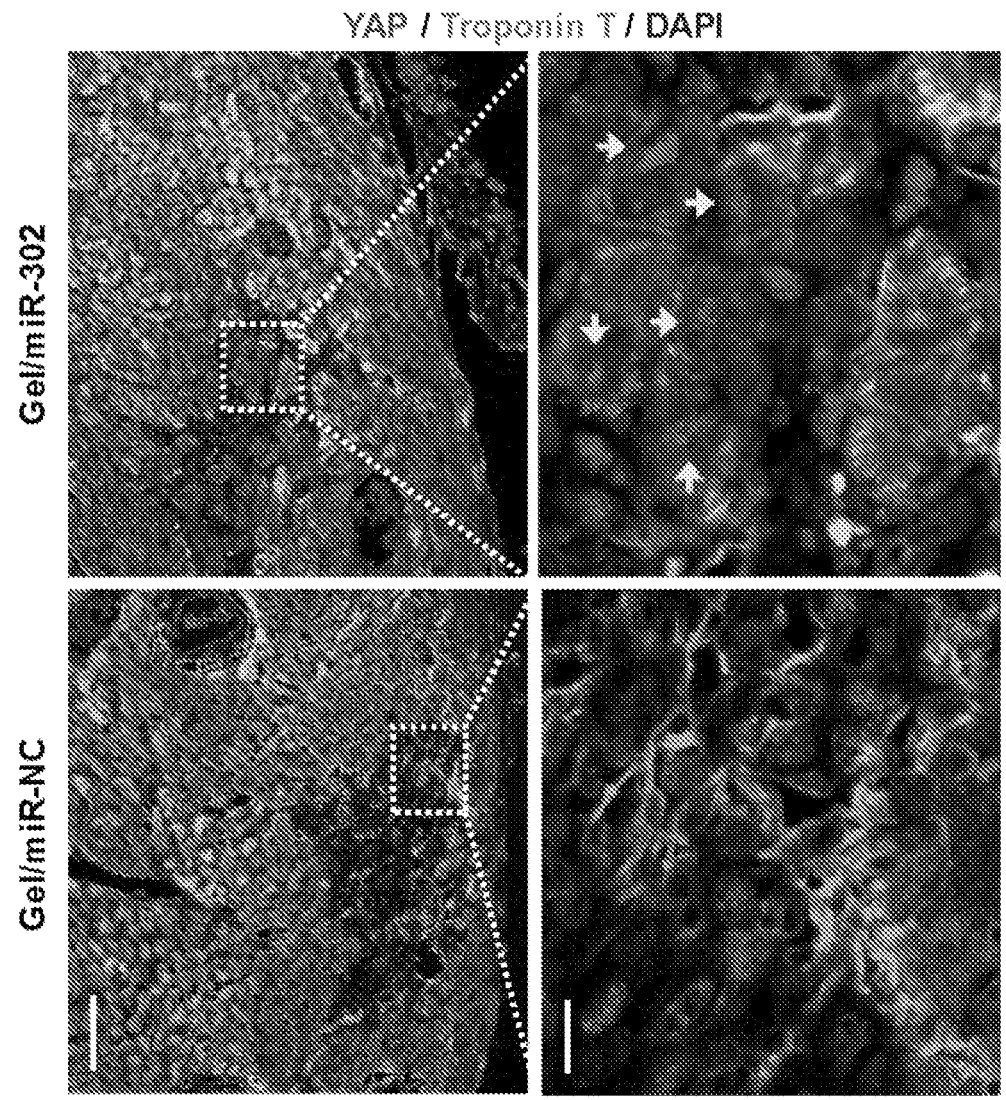
FIG. 14A. Sections were co-stained with Yap after five days post treatment with gel/miR-NC or gel/miR-302.
Figure 14B:
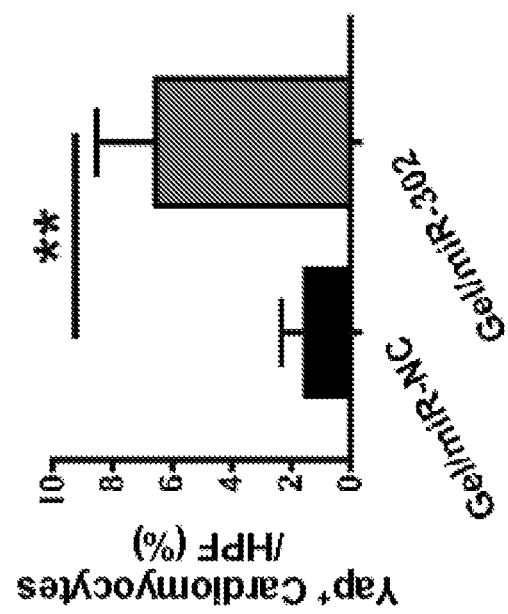
FIG. 14B. Quantification of Ki67 in HPFs surrounding both injection sites for a minimum of three mice per group. Sections demonstrate increased total Yap in gel/miR-302 treated groups; in cells with Yap (yellow arrows), it is localized to the nucleus to suggest its interaction with nuclear transcription factors to promote proliferation (mean±SD, n=3 animals per group, **p<0.01.)
Figure 15:
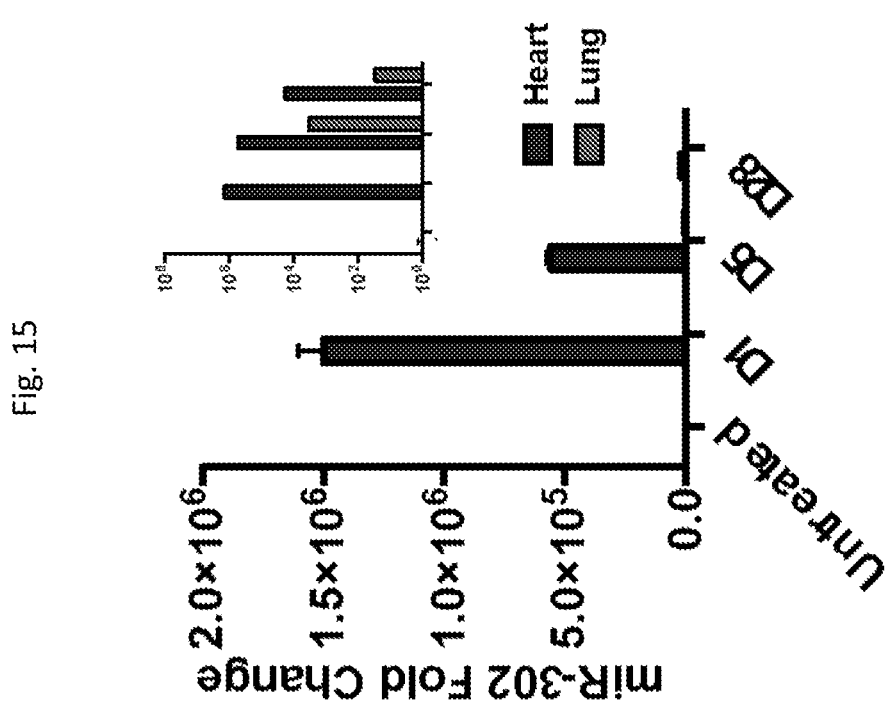
FIG. 15. miR-302 expression in heart and lung after gel/miR-302 injection. Two injections were made inferolateral to the proximal LAD in mouse hearts without infarcts. At D1, D5 and D28, organs were enzymatically digested to harvest total RNA. qPCR was used to quantify total miR-302 relative to untreated mice to demonstrate sustained miR-302 in the heart after injection with gel. Inset is the same graph plotted on a log scale, demonstrating persistent expression of miR-302 out to 28 days with minimal expression in the lung.

Gel/miR-302 injections significantly increased Ki67+, pH3+, and Aurora B+cardiomyocytes around the site of injection compared to controls (FIG. 3c). Of note, whereas PBS/miR-302 injections minimally increased cardiomyocyte proliferation (FIG. 13.), gel/miR-302 assemblies further improved cardiomyocyte proliferation with as many as ~6% (FIG. 3d), ~2% (FIGS. 3e) and ~1% (FIG. 3f) of cardiomyocytes in fields surrounding injection sites stained positive for Ki67, pH3 and Aurora B, respectively. Injections with control miRNA led to very low levels (<1%) of Ki67, pH3 and Aurora B. To confirm that these cardiomyocytes were proliferating through inhibition of Hippo signaling, sections were also stained for Yap. In miR-302 treated sections, there was increased total Yap that localized to the nucleus in support of Yap dephosphorylation and nuclear localization secondary to miR-302 stimulation (FIG. 14).

Example 7

Clonal Proliferation in Confetti Mouse Model

To validate this therapy for myocardial infarction, we examined cardiomyocyte division after myocardial infarction and gel/miR-302 injections. Lineage tracing experiments were done using the R26R-Confetti mouse model, a stochastic, multicolor Cre-reporter construct with loxP-flanked GFP, YFP, RFP and CFP (FIG. 4A).

Mice were obtained by breeding Myh6-MerCreMer and R26R-Confetti reporter mice.

```
Primers to genotype My6-MerCreMer:
Forward:
                              (SEQ ID NO: 20)
CGTTTTCTGAGCATACCTGGA Reverse:
                              (SEQ ID NO: 21)
ATTCTCCCACCGTCAGTACG Primers to genotype R26RConfetti:
Forward:
                              (SEQ ID NO: 22)
AAAGTCGCTCTGAGTTGTTAT Reverse:
                              (SEQ ID NO: 23)
CCAGATGACTACCTATCCTC
```

Intraperitoneal tamoxifen (6.7 mg/kg) single injection was used to induce stochastic labeling of cardiomyocytes in Myh6-MerCreMer/R26R-Confetti mice. Doses were titrated to ensure low levels of cardiomyocyte labeling so that individual clones could be identified. Two weeks after tamoxifen injection, hearts were accessed by thoracotomy and the left ventricle was infarcted by ligation of the left anterior descending artery as described below. Mice were randomized to receive gel/miR-302 or gel/miR-NC (2×5 µL) injections lateral to the infarct in the border zone. 28 days post surgery and miR302 injection, mice were euthanized to collect tissues. The hearts were fixed overnight with 2% paraformaldehyde (PFA). After 24 hours, hearts were then transferred to 50% OCT, followed by continuous incubation with 100% OCT. Then hearts in OCT were frozen with dry ice and kept in −80° C. until sectioning. For WGA staining, sections were rehydrated and then incubated for 1 h at room temperature with WGA conjugated to Alexa Fluor-647 (Life Technologies) in PBS. Slides were then rinsed in PBS and mounted in Vectashield.

To validate this therapy for myocardial infarction, we examined cardiomyocyte division after myocardial infarction and gel/miR-302 injections. Lineage tracing experiments were done using the R26R-Confetti mouse model, a stochastic, multicolor Cre-reporter construct with loxP-flanked GFP, YFP, RFP and CFP (FIG. 4A). For cardiomyocyte lineage tracing, R26R-Confetti mice were bred with aMHC-MerCreMer mice that express a tamoxifen-inducible Cre recombinase downstream of a cardiac specific alpha-myosin heavy chain promoter. This system allows for the stochastic labeling of exclusively cardiomyocytes in a tamoxifen-dependent fashion. By labeling individual cardiomyocytes, clonal increases from cardiomyocyte division can be observed over time in response to gel/miR-302 treatment by counting cells labeled with a unique fluorophore protein.

Figure 16A:
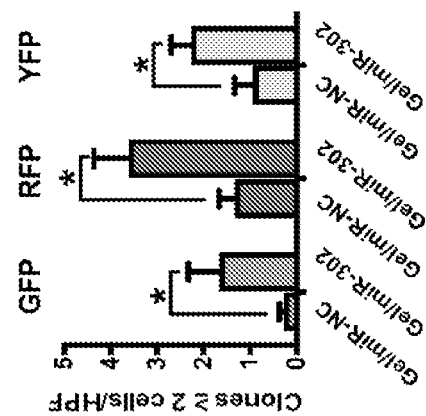
FIG. 16A Fluorescently-labeled cells were identified in border zones of infarcts with clones neighboring each other in gel/miR-302 treated sections. Neighboring nGFP, RFP and YFP cells are magnified to demonstrate clones. Scale bar: 50 μm.
Figure 16A:
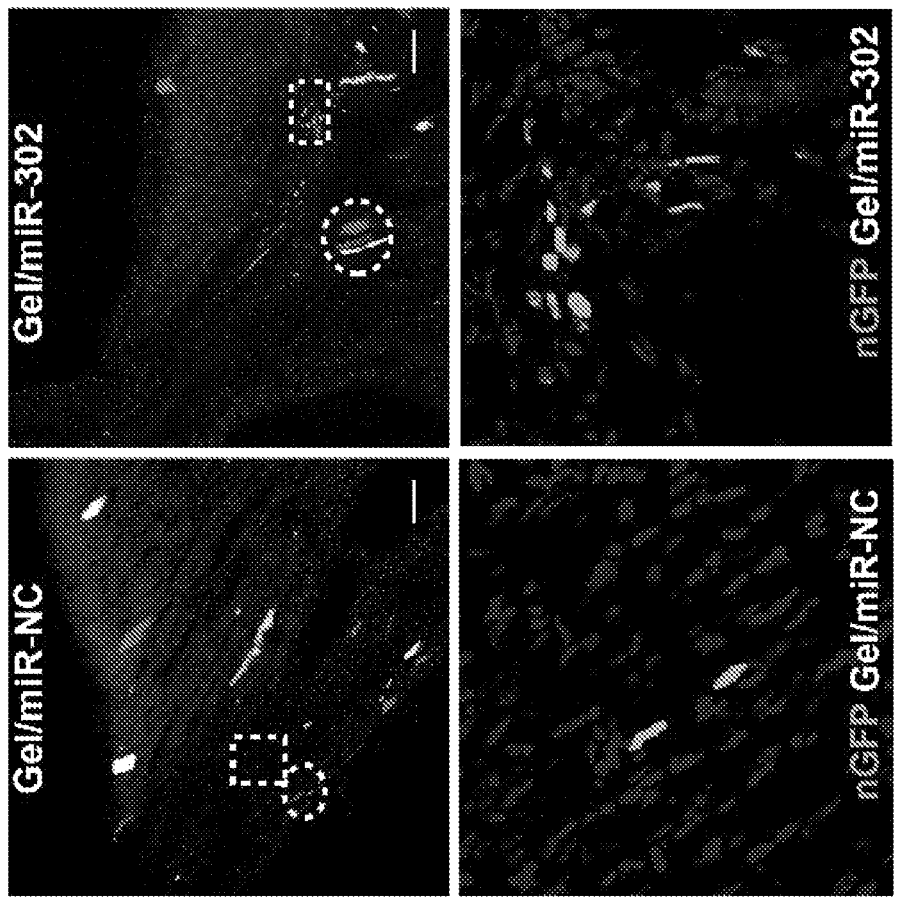

Tamoxifen doses were titrated to ensure low levels of Myh6+cardiomyocyte labeling so that individual clones could be identified. Following tamoxifen injections, hearts were infarcted by ligation of the left anterior descending artery and randomized to receive gel/miR-302 or gel/miR-NC (2×5 µL) injections to the left and right of the infarct in the border zone. At four weeks, hearts were explanted and observed macroscopically (FIG. 4c), where gel/miR-302 injected hearts were strongly labeled near injection sites when compared to controls. Further analysis with confocal imaging revealed expression of nGFP, RFP, and YFP in adult hearts injected with both gel/miR-NC and gel/miR-302 (FIG. 16a).

Figure 16B:
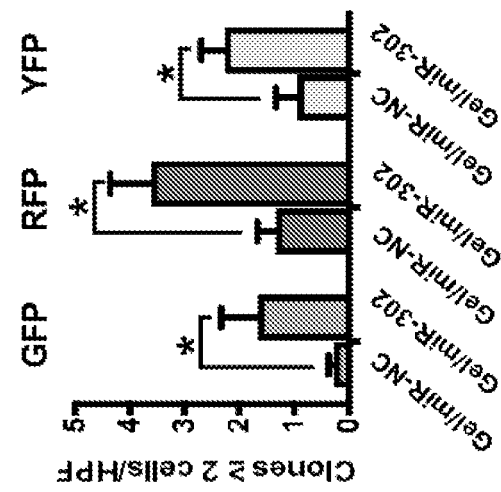
FIG. 16B. Quantification of clones suggesting increased clones in gel/miR-302 treated groups for all three fluorescent reporter proteins. A clone is defined as a minimum of two neighboring cells within 50 μm of each other.
Figure 16B:
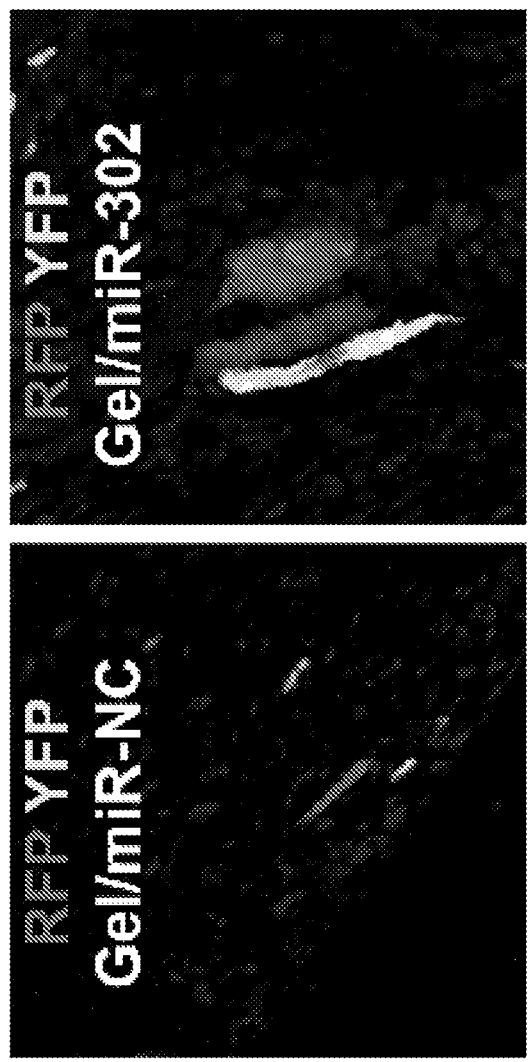
Figure 16C:
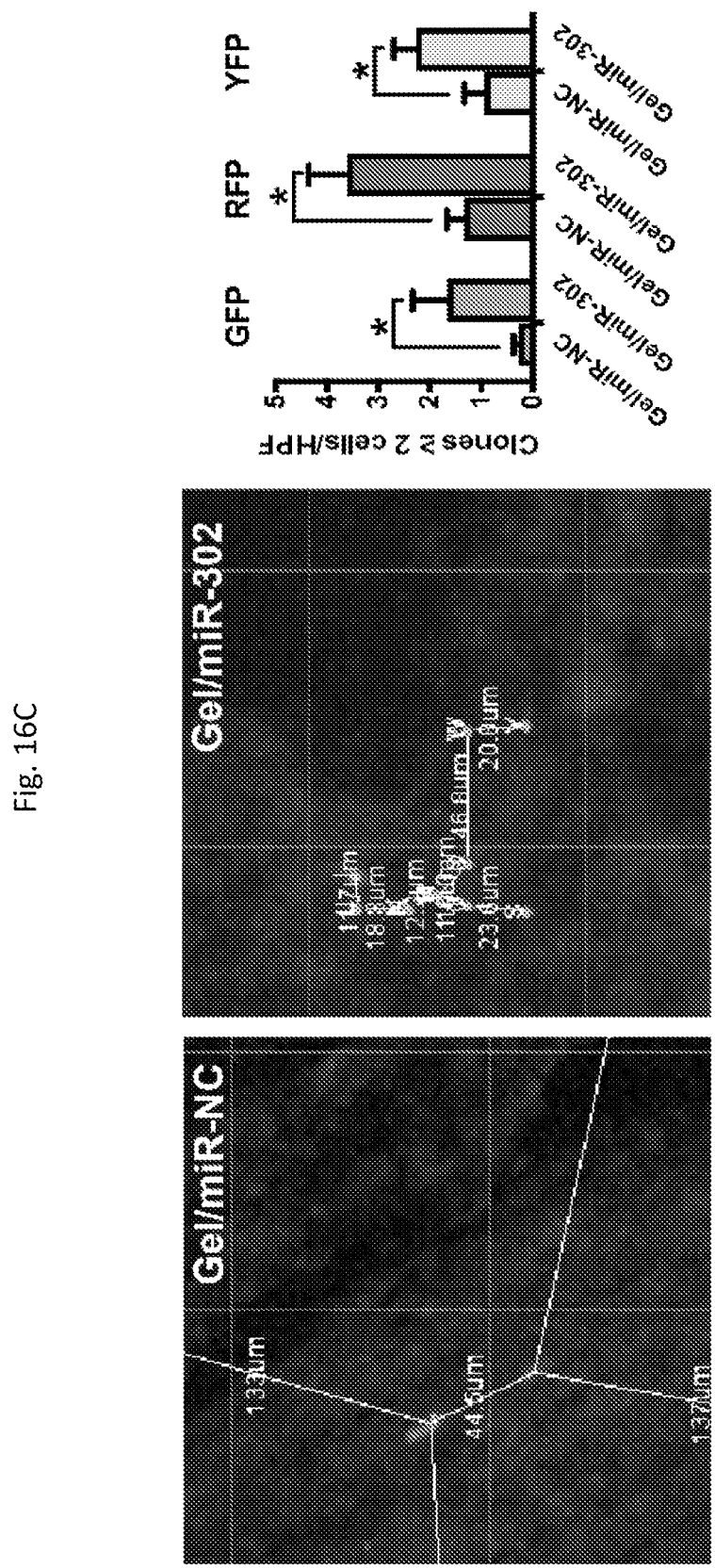
FIG. 16C. nGFP cells were found within 50 μM of each other gel/miR-302 sections, whereas they were greater than 100 μM apart in gel/miR-NC sections. Measurements were performed by IMARIS from 3D confocal images.

Clonal cardiomyocytes expressing nGFP, RFP, and YFP were clearly identified in miR302-injected hearts and few clones were observed with control miRNA injection (FIG. 16b). Among labeled cardiomyocytes, multiple clusters expressing nGFP were detected in gel/miR-302 injected hearts and localized to the border zone of the infarction (FIG. 16a). The average distance between nGFP cells was significantly lower in gel/miR-302 treated groups, suggesting that these cells were derived from a common single cell (FIG. 10c).

Further analysis with Wheat Germ Agglutinin (WGA) staining to identify cell membranes showed fluorescent cells within 50 µm were mostly contiguous in gel/miR-302 treated groups but not in gel/miR-NC groups (FIG. 5a). In gel/miR-NC groups, distant cells (>50 µm) were often interspersed by unlabeled cardiomyocytes. Using 50 µm as a standard, we quantified the number of cells to a single clone for nGFP, RFP, and YFP across all sections of the heart in the border zone of infarcts. Gel/miR302-injected hearts had a significant increase in the number of cells per clone (as many as 8) to suggest that these cells were derived from a common parent cell that had divided (FIG. 5b).

Example 8

Cardiac Function After MI and gel/miR-302 Injection

Figure 6A:
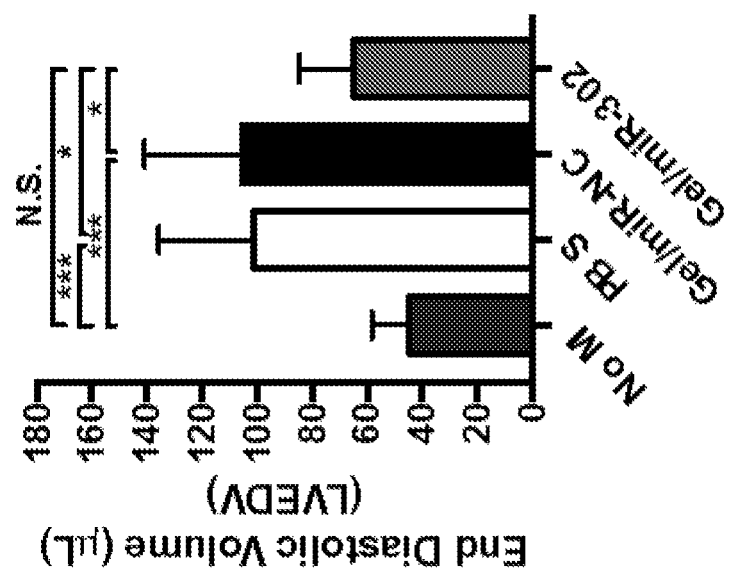
FIG. 6A. End diastolic and FIG. 6B end systolic volumes at 4 weeks after myocardial infarction in mice treated with PBS, gel/miR-NC, or gel/miR-302 by B-mode echocardiography. Volume increases were significantly decreased in gel/miR-302 treated groups compared to controls.
Figure 6B:
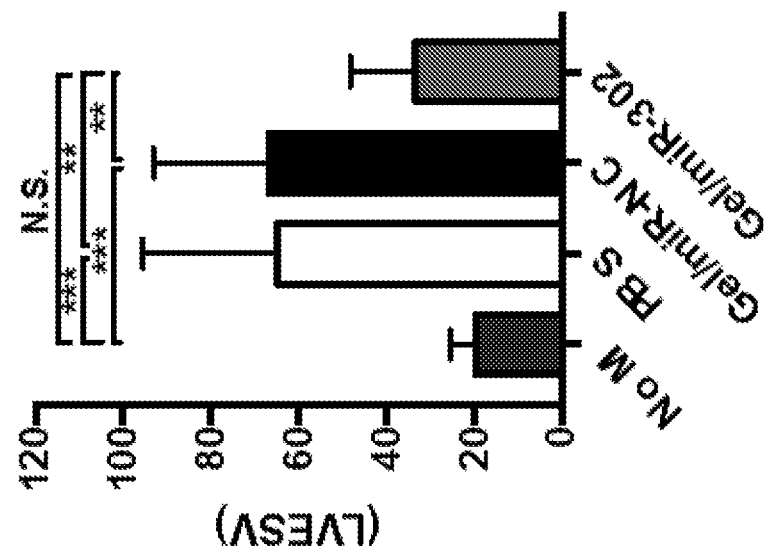
FIG. 6. Functional outcomes after myocardial infarction.
FIG. 6C. Ejection fraction and FIG. 6D fractional shortening at 4 weeks after myocardial infarction by echocardiography. Neither ejection fraction nor fractional shortening of gel/miR-302 treated mice were significantly different from non-infarcted mice. All groups were compared through 1-way ANOVA (Mean±SD, no MI, n=10; PBS, n=13; gel/miR-NC, n=10, gel/miR-302, n=12. $*p<0.05$ $p<0.01$ $*p<0.001$).
FIG. 6E. Representative Mason's trichrome sections demonstrating cardiac volume improvement at 28 days. Sections are arranged from ligation to the apex to visualize changes in tissue remodeling. Scale bar=2 mm.
FIG. 6F M-mode echocardiographs of left ventricular anterior and posterior walls demonstrating diminished motion in anterior wall of gel/miR-NC treated mice with improvement in gel/miR-302 treated mice.
Figure 6D:
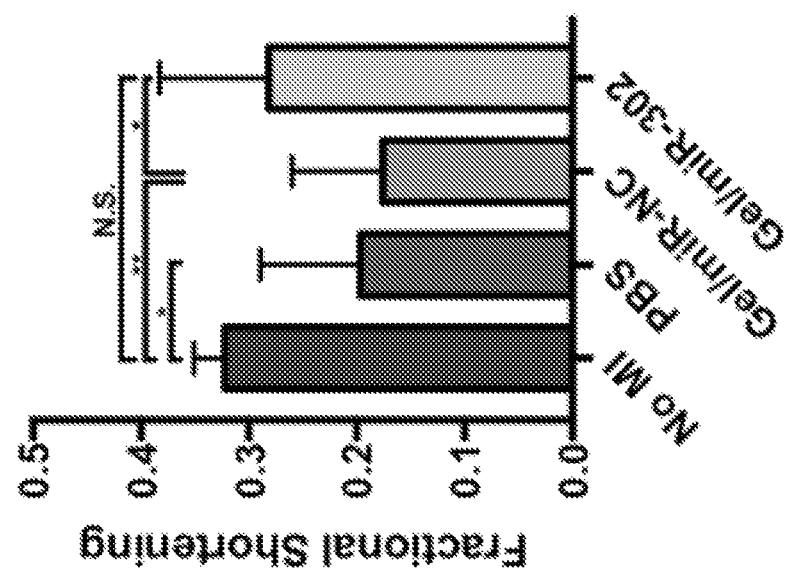
Figure 6E:
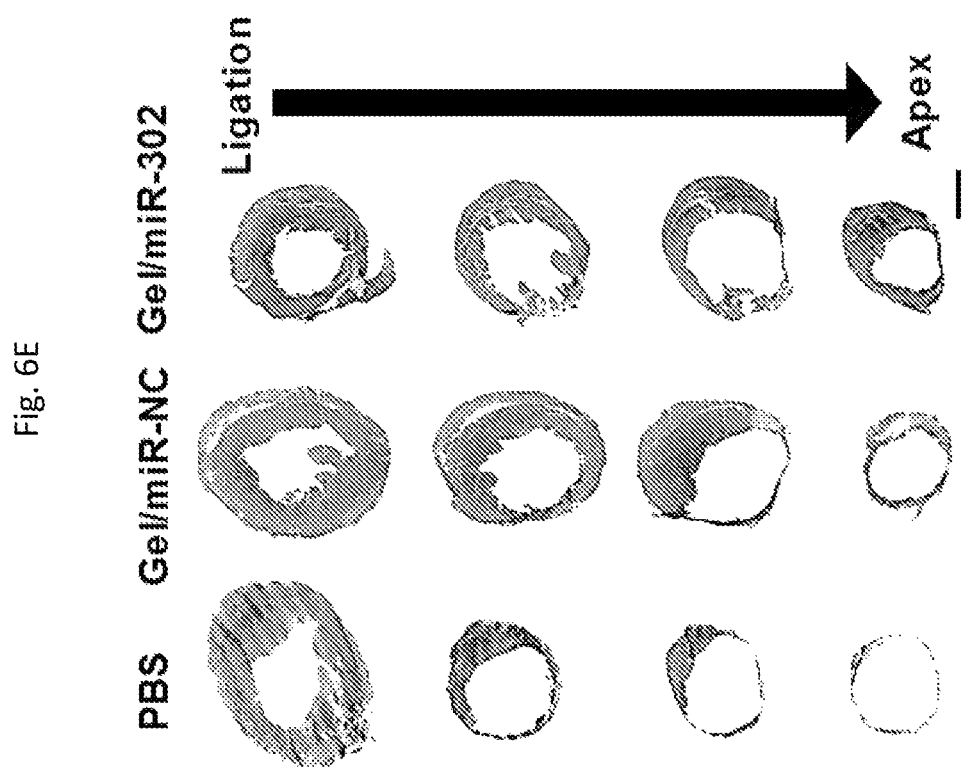
Figure 6F:
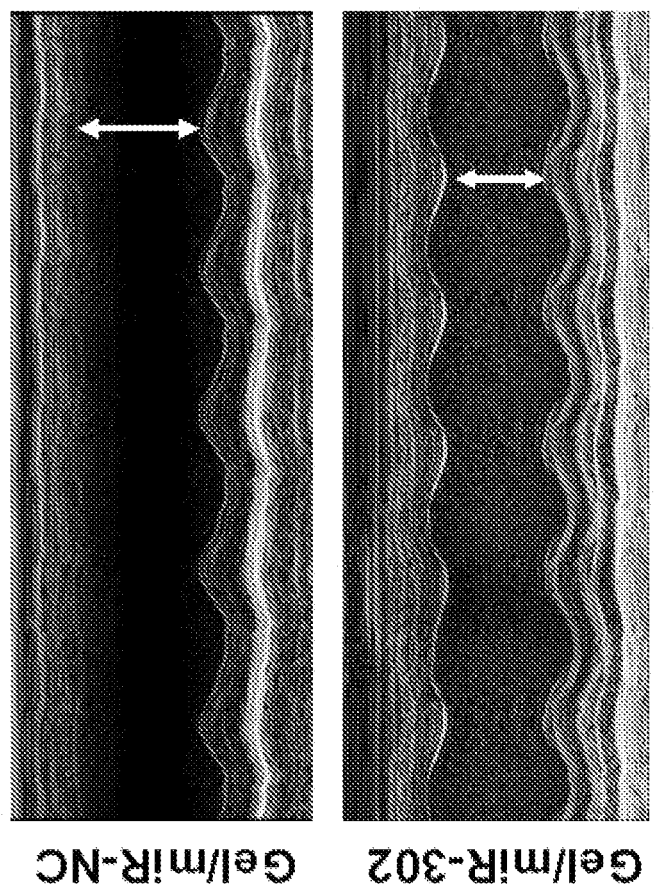

Recognizing the ability of gel/miR-302 to induce both cardiomyocyte proliferation in non-infarcted tissue and to increase cell number after infarction, we examined the ability for gel/miR-302 to improve physiological outcomes after MI by echocardiography. Adult mice were randomized to receive gel/miR-302, gel/miR-NC, or PBS injection after infarction caused by LAD ligation. After four weeks, cardiac function was analyzed through echocardiography and measurements of left ventricular end diastolic volume (LVEDV), left ventricular end systolic volume (LVESV), ejection fraction (EF), and fractional shortening (FS) were made. Gel/miR-302 treated mice had reduced cardiac remodeling, demonstrated by reductions in LVEDV and LVESV, measures of cardiac volumes at the beginning and end of a single contraction, respectively, compared to PBS or gel/miR-NC controls (FIG. 6A,B). LVEDV and LVESV of gel/miR-302 treated animals were not significantly different from non-infarcted mice. From a functional perspective, whereas PBS and gel/miR-NC treated animals had significantly reduced EF and FS, EF and FS of gel/miR-302 treated animals were not significantly different from non-infarcted mice (FIG. 6C,D). Mason's trichrome staining performed on tissue sections at four weeks also corroborated the volume changes from echocardiography, where the smallest left ventricular areas from axial sections were found with gel/miR-302 treatment (FIG. 6E). Representative 1-D echocardiographic M-mode measurements of anterior and posterior wall movement in the left ventricle are shown (FIG. 6F), which illustrate improved anterior wall movement and decreased systolic and diastolic inner diastolic diameters in gel/miR-302 treated mice.

The invention claimed is:

1. A guest-host hydrogel for controlled, local delivery of an miR-302 mimic to contractile tissue in vivo comprising
   (a) a shear-thinning and self-healing guest-host hydrogel, which comprises
      (i) a β-cyclodextrin-modified hyaluronic acid (HA) polymer (CD-HA) and
      (ii) an adamantane-modified HA polymer (AD-HA); and
   (b) a cholesterol-modified miR-302 mimic, wherein the miR-302 minic comprises (A) cholesterol-modified miR-302b mimic comprising a guide strand as set forth in SEQ ID NO: 16 and a passenger strand as set forth in SEQ ID NO: 17 and (B) a cholesterol-modified miR-302c mimic comprising a guide strand as set forth in SEQ ID NO: 18 and a passenger strand as set forth in SEQ ID NO: 19, and the cholesterol modifications are at the 5'-end of each passenger strand; and
   wherein the dose of the cholesterol-modified miR-302 mimic does not disrupt the guest-host hydrogel interaction, and wherein the CD-HA and AD-HA polymers are not covalently cross-linked to each other.

2. The guest-host hydrogel of claim 1 wherein about 60% of the cholesterol-modified miR-302 mimic is released within 10 days, as determined by in vitro assay.

3. The guest-host hydrogel of claim 1, wherein about 25% of hyaluronic acid disaccharide repeats in the the CD-HA polymer are modified with β-cyclodextrin and/or about 25% of hyaluronic acid disaccharide repeats in the the AD-HA polymer are modified with adamantane.

4. The guest-host hydrogel of claim 1, wherein the cholesterol-modified miR-302b is derived from SEQ ID NO: 11, and the cholesterol-modified miR-302c is derived from SEQ ID NO: 12.

5. The guest-host hydrogel of claim 1, wherein at least 80% of the cholesterol-modified miR-302 mimic is released from the gel by 21 days.

6. The guest-host hydrogel of claim 1, wherein the cholesterol-modified miR-302b and cholesterol modified miR-302c are present in equimolar amounts.

7. The guest-host hydrogel of claim 1, wherein gel erosion in the presence of the miR-302 mimic is within about 10% of gel erosion in the absence of the miR-302 mimic, after 14 days, as measured by uronic acid assay measuring total HA degradation.

8. The guest-host hydrogel of claim 1, wherein the CD-HA polymer has about 20 to about 25% of its hyaluronic acid disaccharide repeats modified with β-cyclodextrin; and the AD-HA polymer has about 20 to about 25% of its hyaluronic acid disaccharide repeats modified with adamantane.

9. The hydrogel of claim 1, wherein the contractile tissue is cardiac tissue.

10. The hydrogel of claim 9 wherein the cardiac tissue is terminally differentiated.

11. A guest-host hydrogel for controlled, local delivery of an miR-302 mimic to contractile tissue in vivo comprising
   (a) a shear-thinning and self-healing guest-host hydrogel, which comprises
      (i) a β-cyclodextrin-modified hyaluronic acid (HA) polymer (CD-HA) and
      (ii) an adamantane-modified HA polymer (AD-HA) wherein the final concentration of polymers is about 5 wt %; and
   (b) a cholesterol-modified miR-302 mimic consisting of
      (i) a cholesterol modified miR-302b sequence derived from SED ID NO:11; and
      (ii) a cholesterol modified miR-302c mimic consisting of a cholesterol-modified miR-302c sequence derived from SED ID NO: 12;
   wherein miR-302b comprises a guide strand as set forth in SEQ ID NO: 16 and a passenger strand as set forth in SEQ ID NO: 17, miR-302c comprises a guide strand as set forth in SEQ ID NO: 18 and a passenger strand as set forth in SEQ ID NO: 19, and the cholesterol modifications are at the 5'-end of each passenger strand;

wherein the cholesterol modified miR-302b and the cholesterol-modified miR-302c are present in equimolar amounts, and wherein the dose of the cholesterol-modified miR-302 mimic does not disrupt the guest-host hydrogel interaction, and wherein the CD-HA and AD-HA polymers are not covalently cross-linked to each other.

12. The guest host hydrogel of claim 11 wherein the cholesterol-modified miR-302b and the cholesterol modified miR-302c are each present at a concentration relative to the total hydrogel volume of about 200 μM to about 250 μM.

13. A method of stimulating cardiomyocyte proliferation in damages cardiac tissue in a subject, comprising locally administering to the damaged cardiac tissue in the subject the guest-host hydrogel according to claim 1.

14. The method of claim 13, wherein administration of the guest-host hydrogel is an intramyocardial injection into the damaged cardiac tissue.

15. The method of claim 13, wherein the damaged cardiac tissue results from a myocardial infarction.

16. The method of claim 13, wherein the CD-HA polymer has about 20 to about 25% of its hyaluronic acid disaccharide repeats modified with β-cylodextrin; and the AD-HA polymer has about 20 to about 25% of its hyaluronic acid disaccharide repeats modified with adamantane.

17. The method of claim 13, wherien about 25% of hyaluronic acid disaccharide repeats in the CD-HA polymer are modified with β-cylodextrin and/or about 25% of hyaluronic acid disaccharide repeats in the AD-HA polymer are modified with adamantane.

18. The method of claim 13, wherein the subject is a human.

* * * * *